(12) United States Patent
Guo et al.

(10) Patent No.: US 7,528,365 B2
(45) Date of Patent: May 5, 2009

(54) CHEMICAL NOISE REDUCTION FOR MASS SPECTROMETRY

(75) Inventors: Xinghua Guo, Groningen (NL); Andries P. Bruins, Groningen (NL); Tom Covey, Richmond Hill, CA (US)

(73) Assignees: Applera Corporation, Framingham, MA (US); MDS Inc., Concord, Ontario (CA)

( * ) Notice: Subject to any disclaimer, the term of this patent is extended or adjusted under 35 U.S.C. 154(b) by 206 days.

(21) Appl. No.: 11/672,101

(22) Filed: Feb. 7, 2007

(65) Prior Publication Data

US 2007/0262253 A1 Nov. 15, 2007

Related U.S. Application Data

(60) Provisional application No. 60/765,809, filed on Feb. 7, 2006.

(51) Int. Cl.
*H01J 49/42* (2006.01)
(52) U.S. Cl. .................................. 250/282; 250/292
(58) Field of Classification Search .............. 250/282, 250/281, 292
See application file for complete search history.

(56) References Cited

U.S. PATENT DOCUMENTS

| 6,140,638 | A | 10/2000 | Tanner et al. |
| 6,781,117 | B1* | 8/2004 | Willoughby et al. ........ 250/281 |
| 7,253,406 | B1* | 8/2007 | Sheehan et al. ............ 250/288 |
| 2003/0044994 | A1 | 3/2003 | Bandura et al. |
| 2003/0213900 | A1 | 11/2003 | Hoyes |
| 2004/0026610 | A1 | 2/2004 | Abou-Shakra et al. |
| 2008/0149824 | A1 | 6/2008 | Miller et al. |

FOREIGN PATENT DOCUMENTS

WO 0016375 A1 3/2000

* cited by examiner

*Primary Examiner*—Kiet T Nguyen
(74) *Attorney, Agent, or Firm*—Kurt Rauschenbach; Rauschenbach Patent Law Group, LLC

(57) ABSTRACT

In various aspects, the present teachings provide systems and methods for reducing chemical noise in a mass spectrometry instrument that use a neutral chemical reagent and one or more mass filters to reduce interfering chemical background ion signals that are generated by ionization sources of mass spectrometers. In various embodiments, the neutral chemical reagent belongs to the class of organic chemical species containing a disulfide functionality.

36 Claims, 37 Drawing Sheets

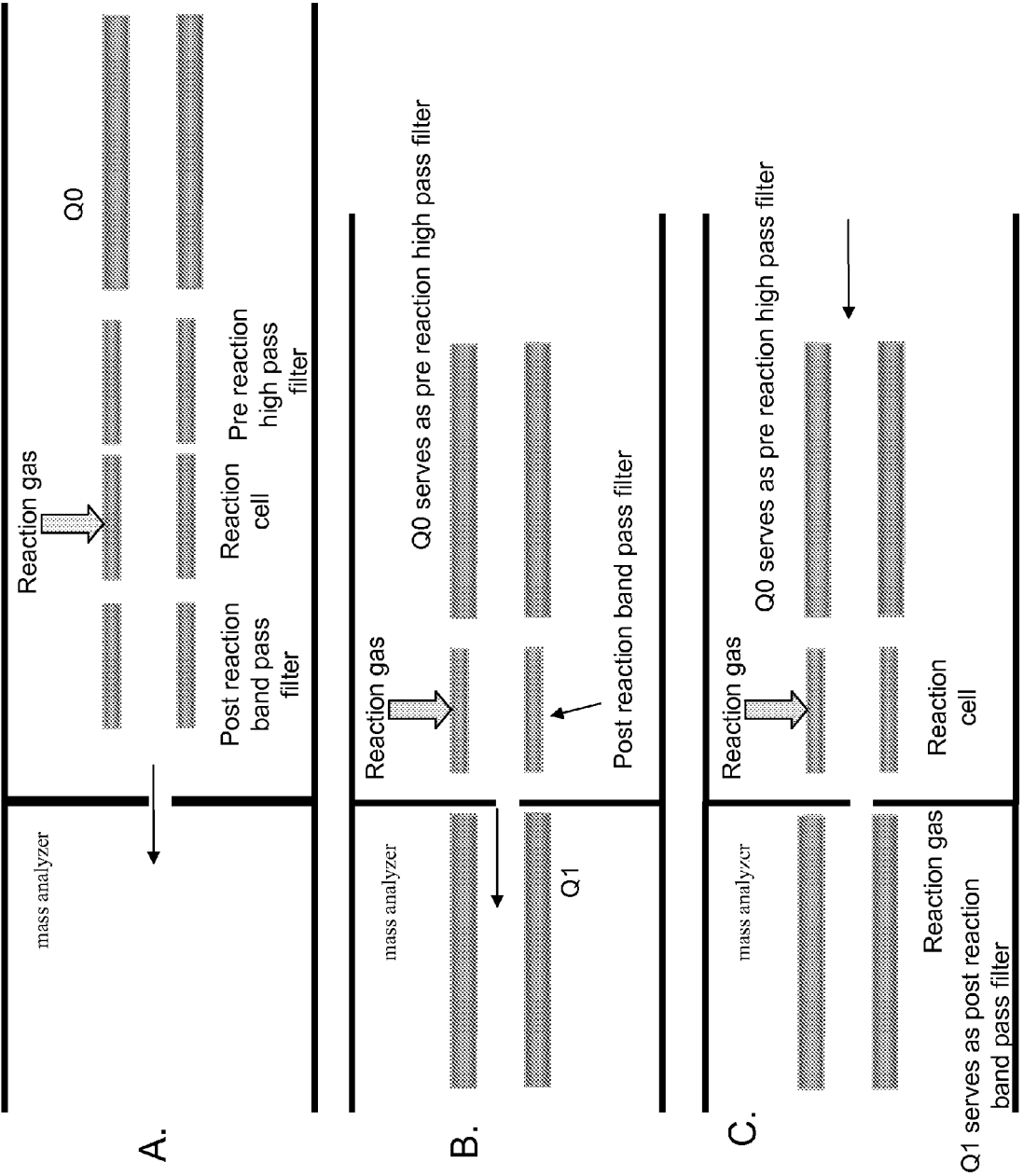
Figures 2A-C

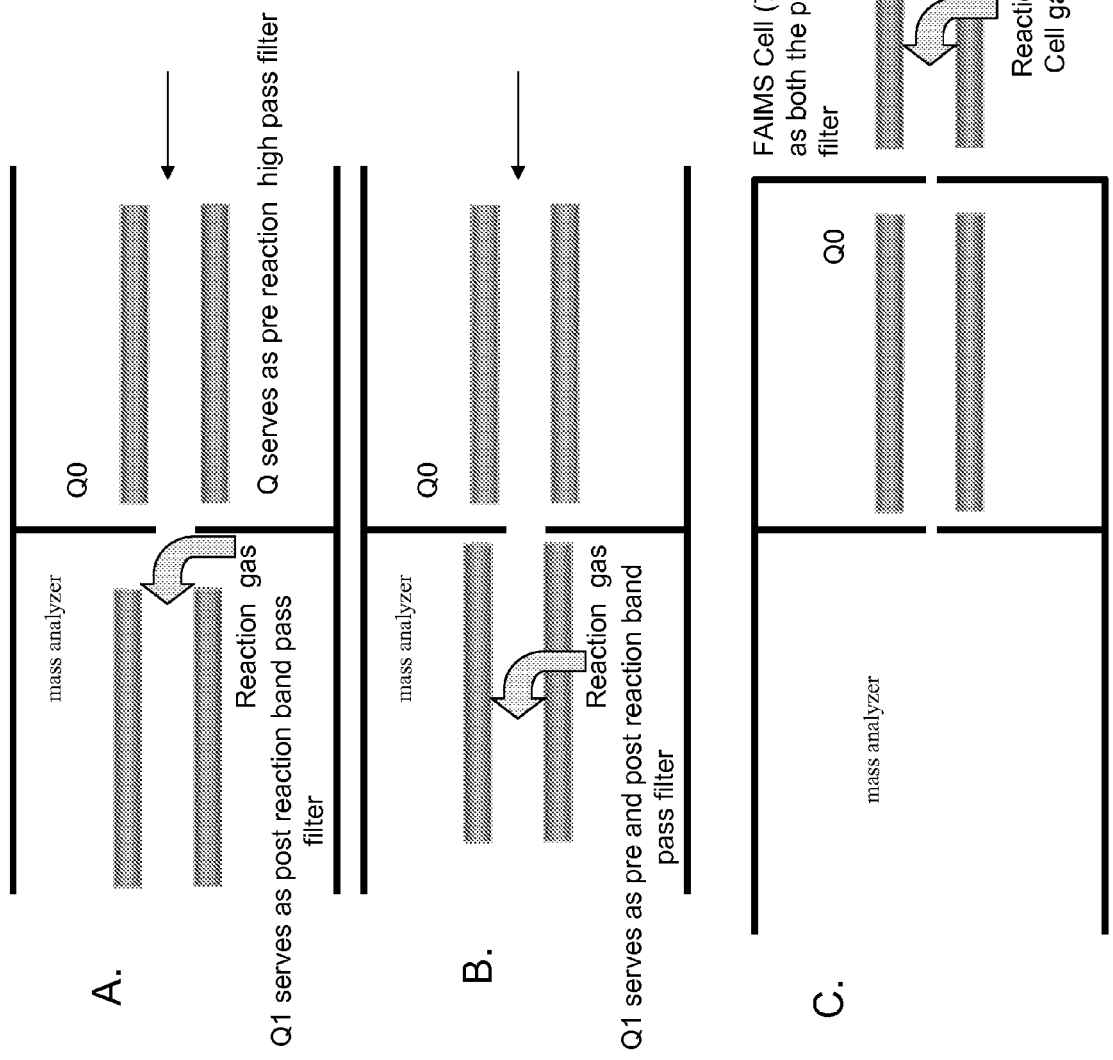

FIGURES 4A-B

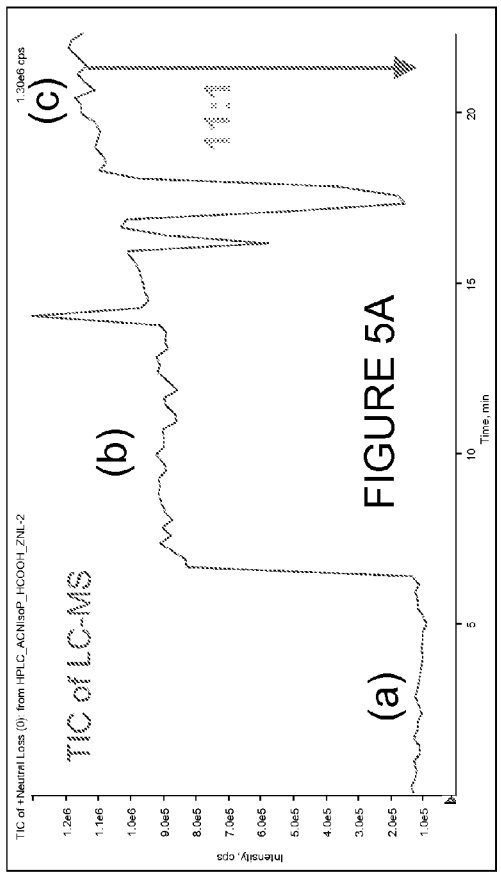
FIGURE 5
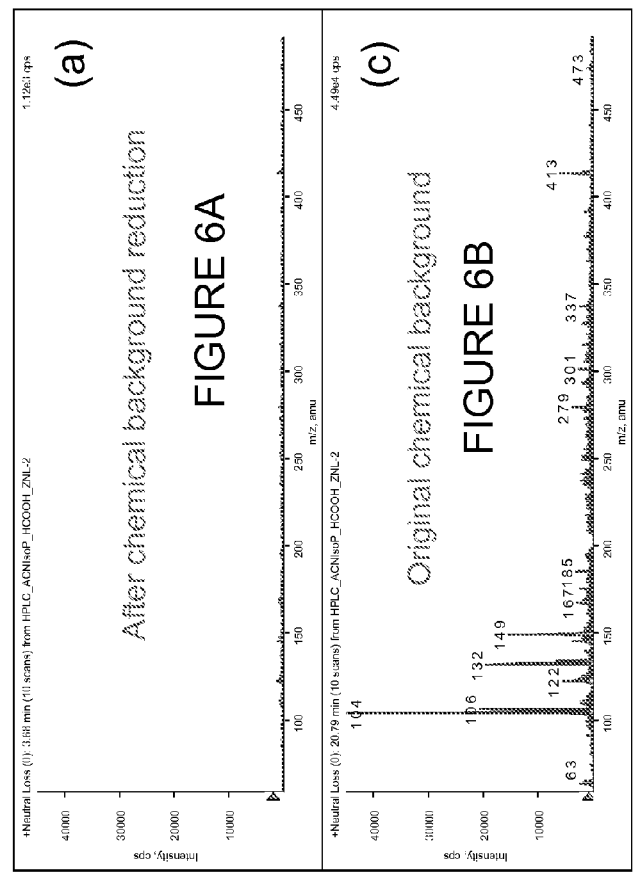
FIGURES 6A-B

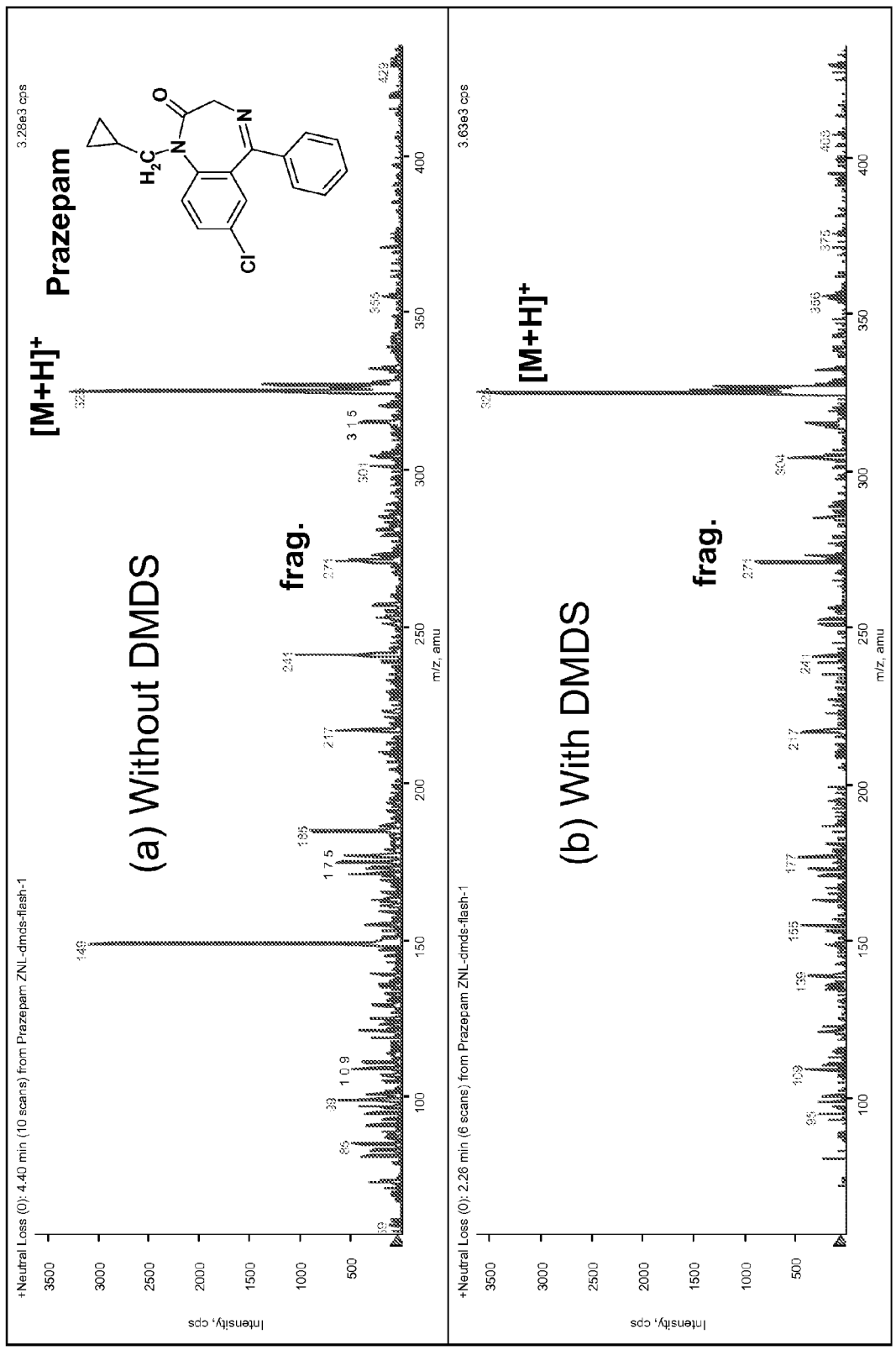
Figures 7A-B

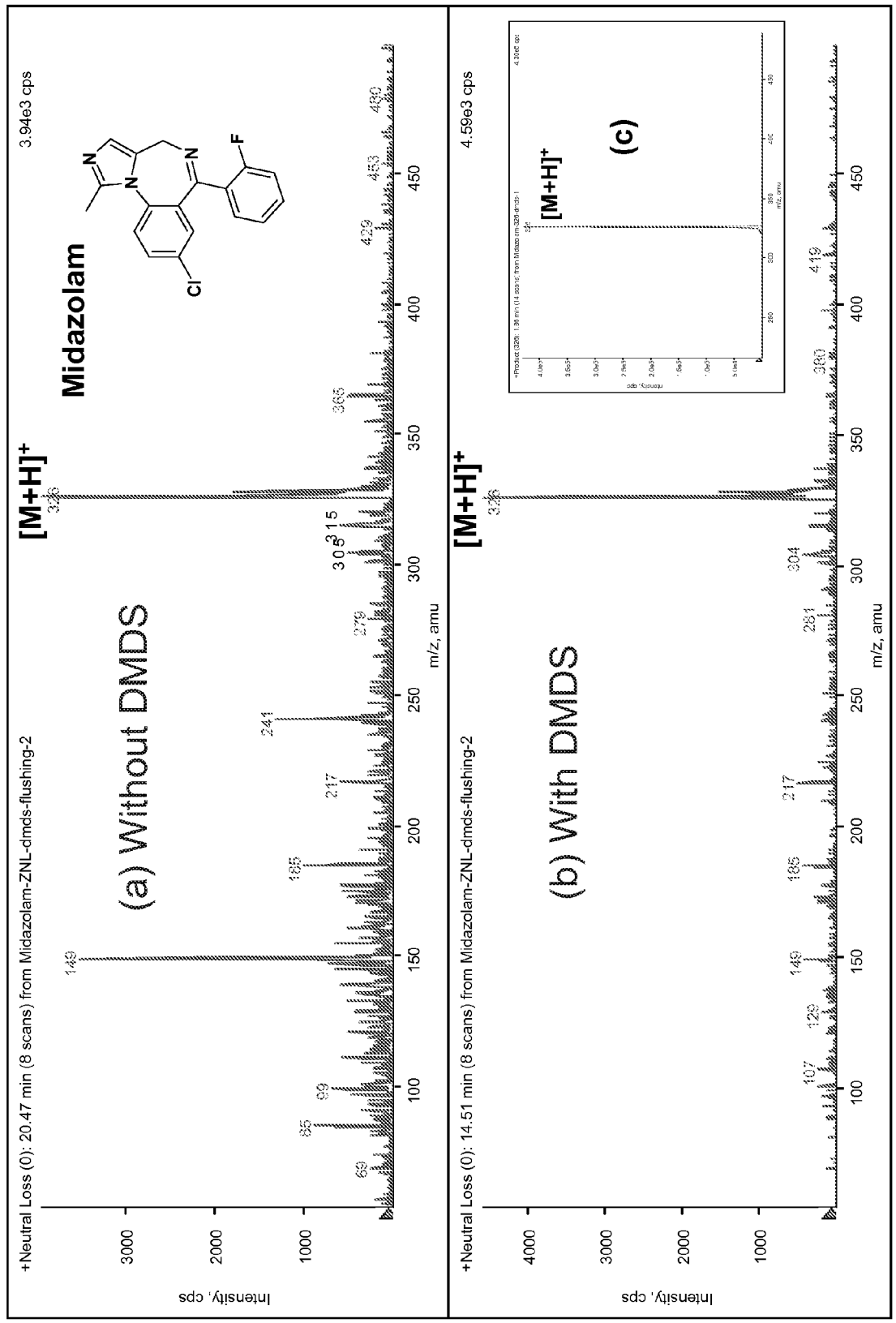
Figures 9A-C

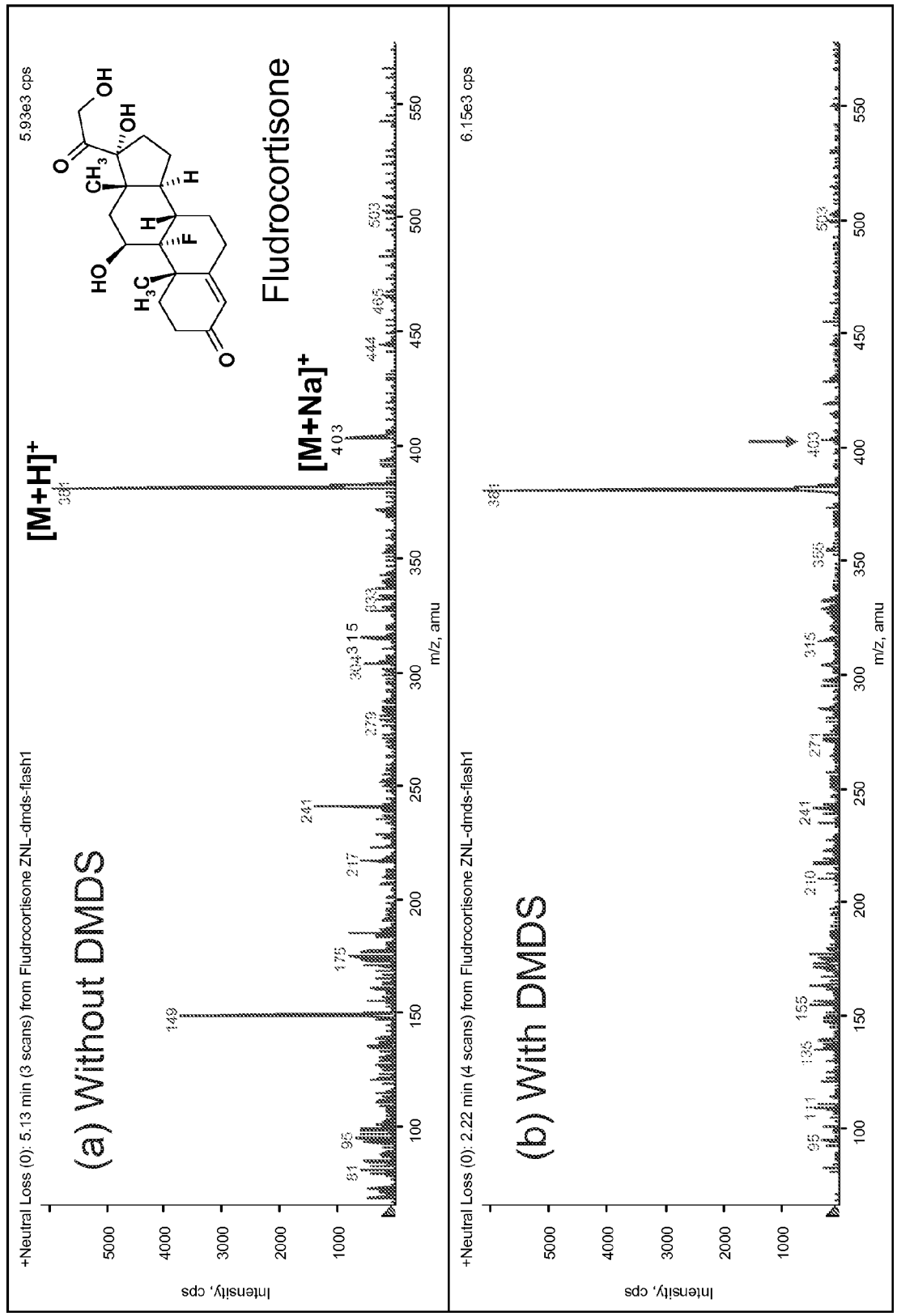
Figures 10A-B

Figures 11A-B

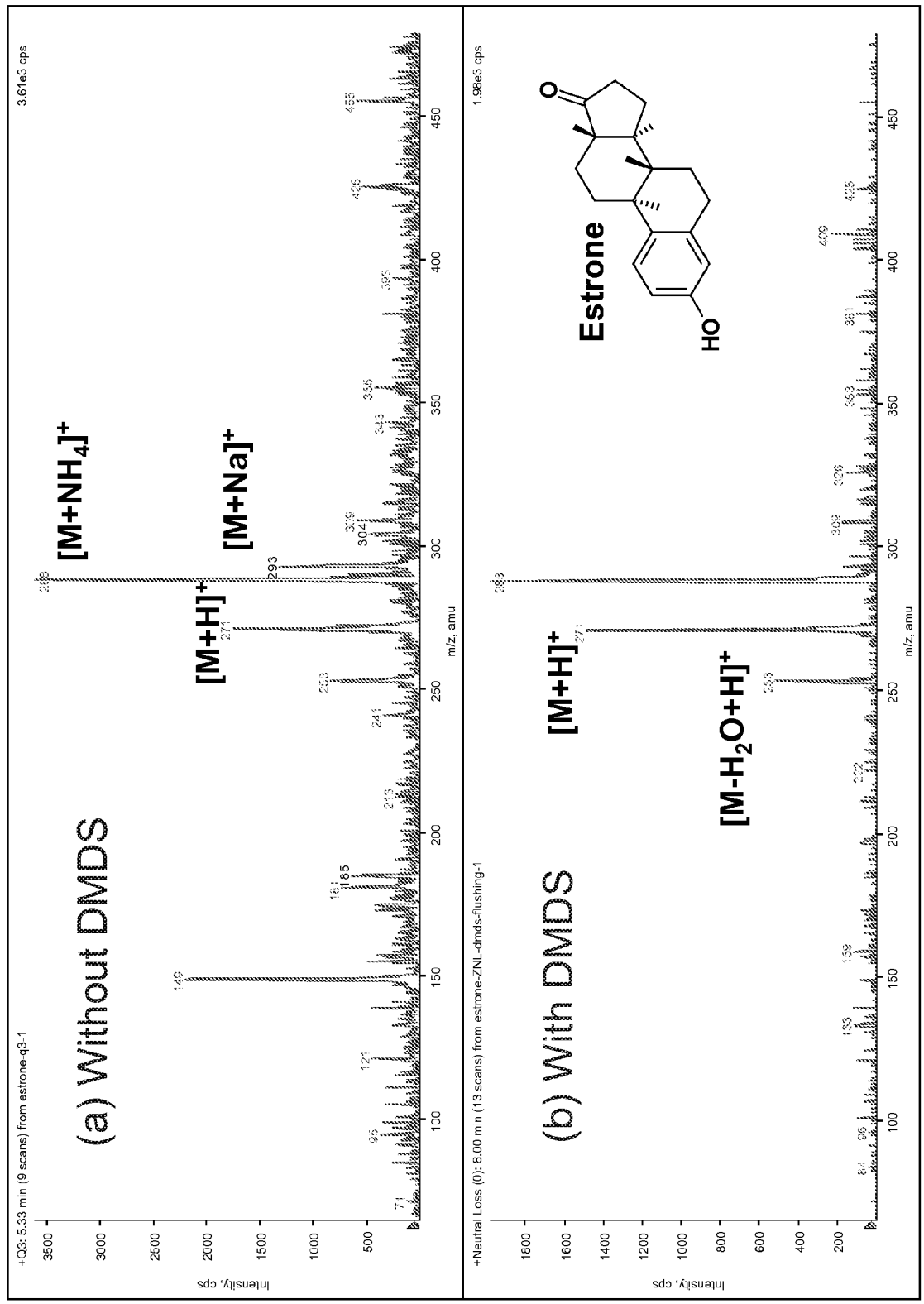
Figures 12A-B

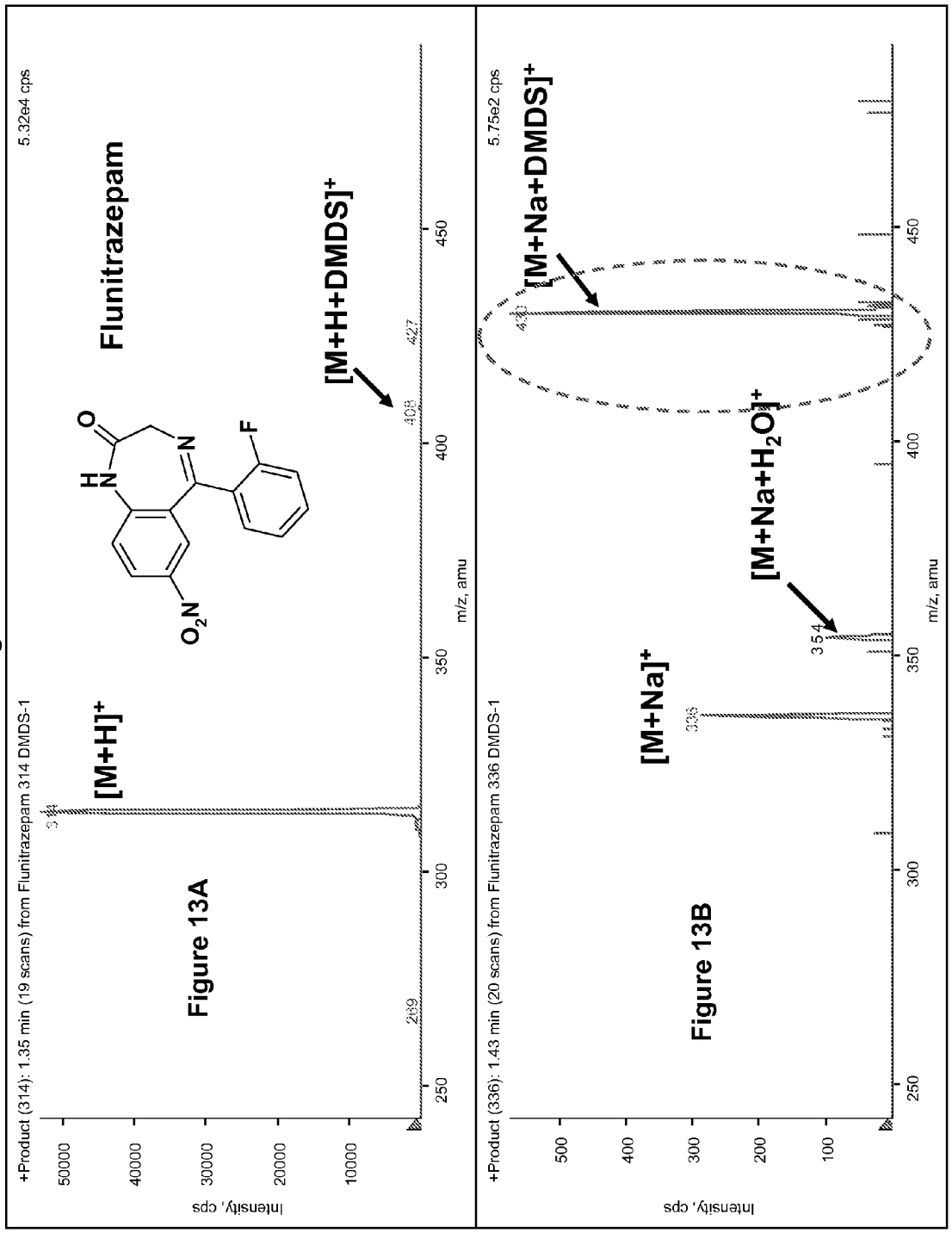
Figures 13A-B

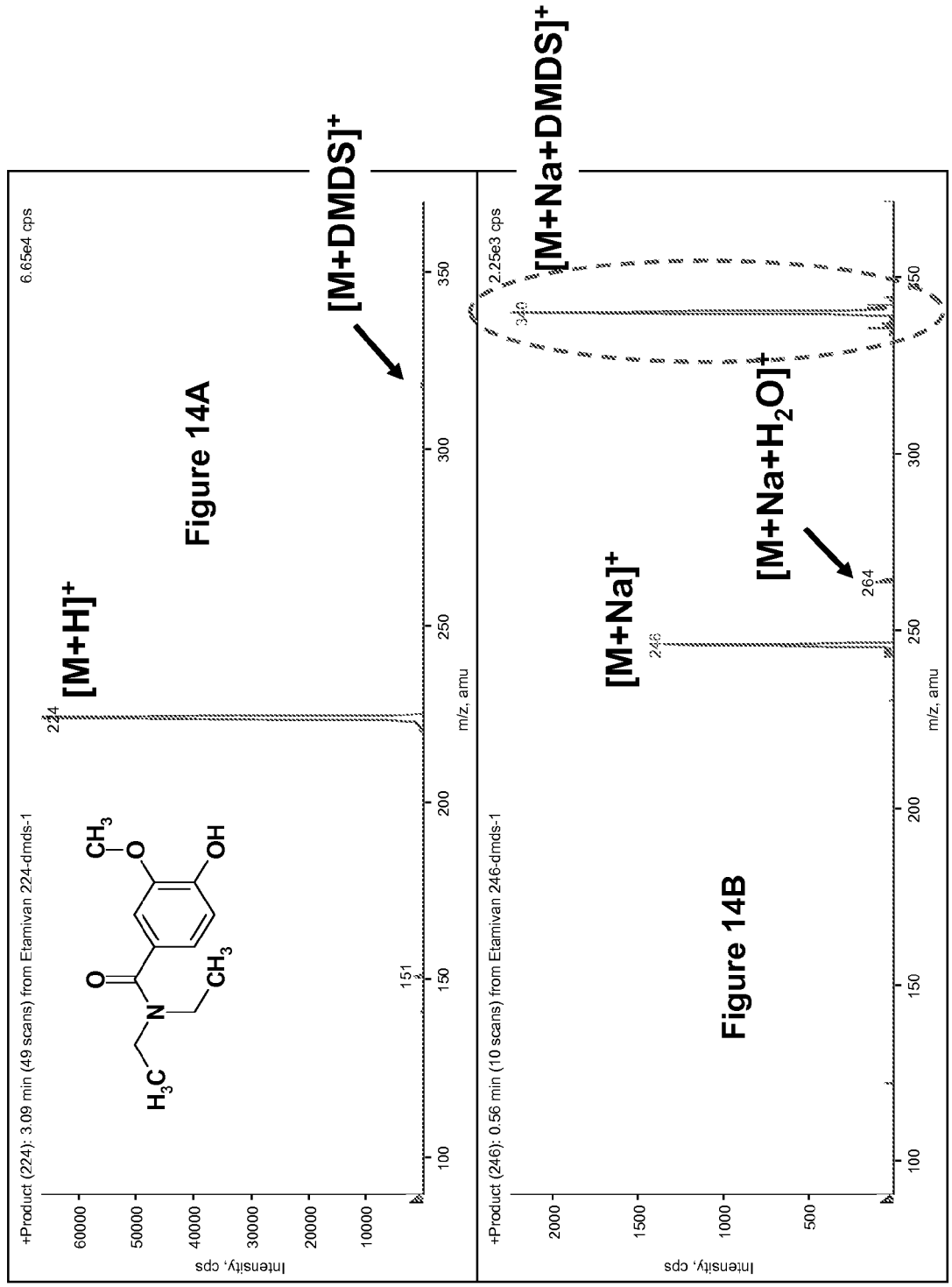
Figures 14A-B

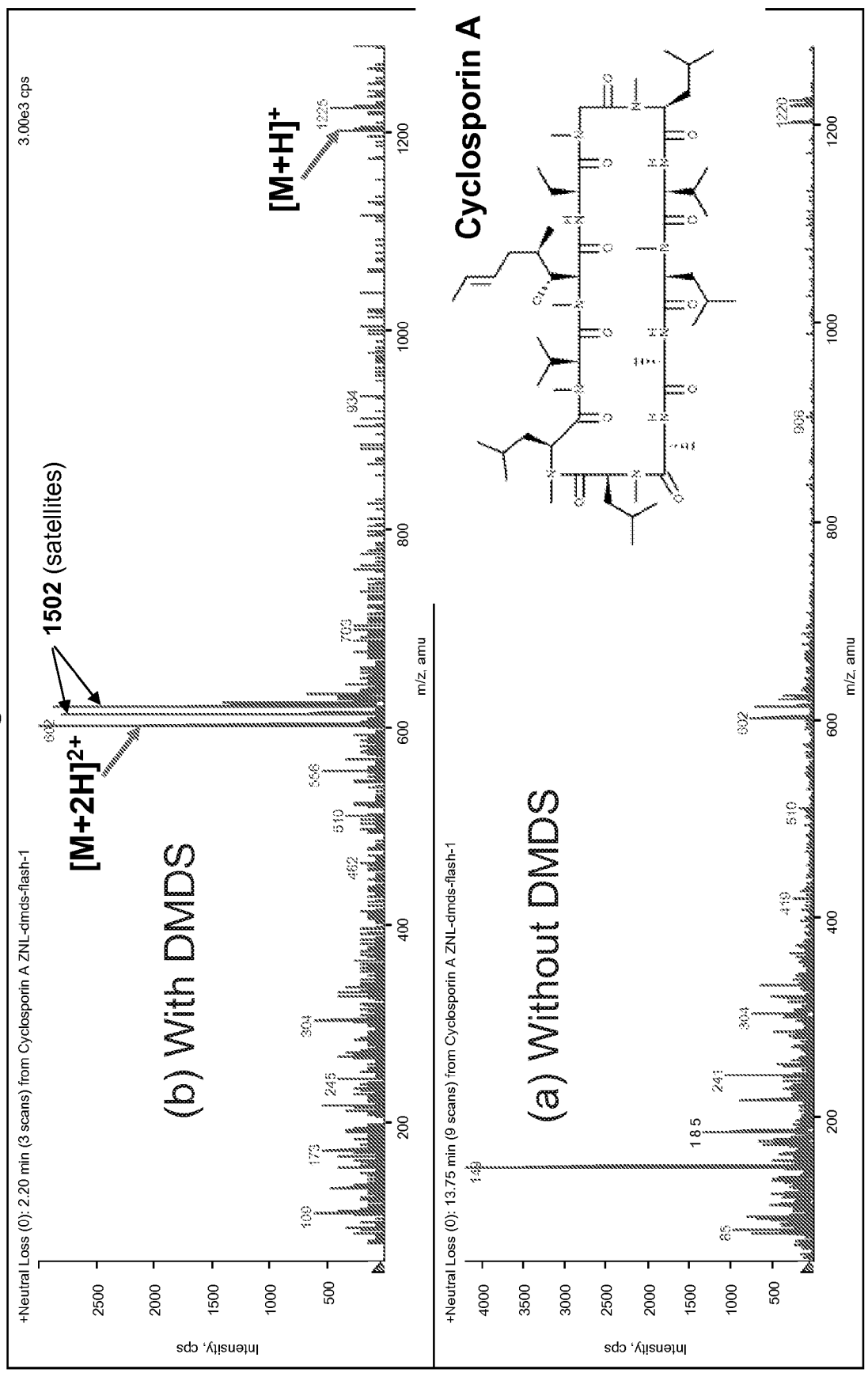
Figures 15A-B

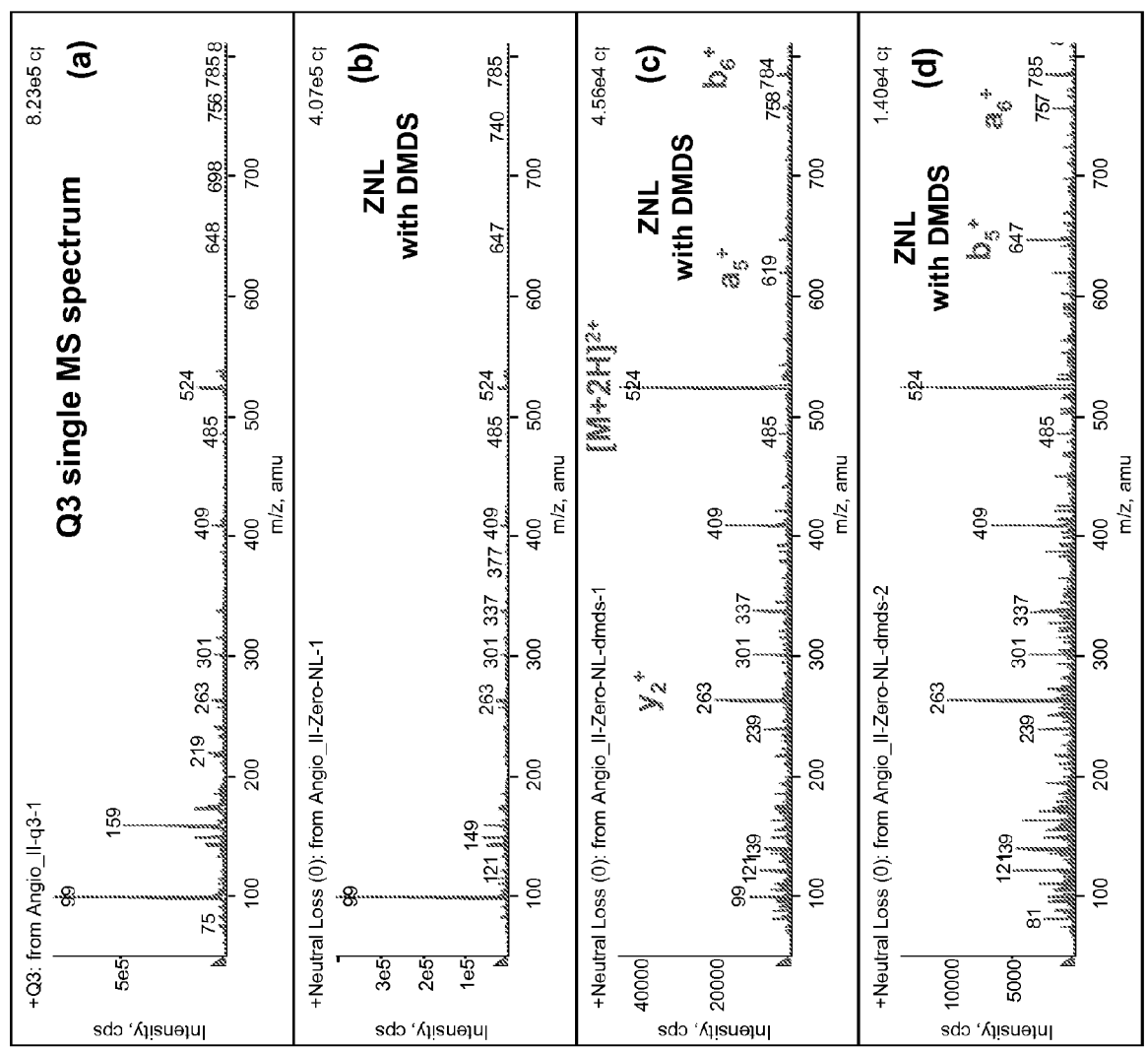
Figures 16A-D

Figure 18

Table 1/3

| # | Compound name | Functional groups, or possible reaction sites | [M+H]+ (%) reactive | [M+Na]+ (%) reactive | Others [ ]+ (%) reactive |
|---|---|---|---|---|---|
| 1 | Ofloxacin | -COOH, t-N- | 362 (15) | | |
| 2 | | t-N- | 318 (3) | | |
| 3 | Norfloxacin | -COOH, t-N-, -NH- | 320 (4) | | 302 (85) |
| 4 | Rifampicin | -CO-NH-, -CO-O-, -C=N-NR$_2$ | 823 (2) | | 791 (0), 694 (0), 399 (0), 726 (15), 748 (0) |
| 5 | Testosterone | -OH, -C=CR-C(R)O | 289 (8) | 311 (70) | 577 (80), 599 (2) |
| 6 | Caffeine | R$_2$N-CO-NR$_2$, R$_2$N-C=N-R | 195 (0) | | |
| 7 | Etamivan | -CO-NR$_2$, ph-OH | 224 (1) | 246 (65) | 447(20), 469(-); 151(20) |
| 8 | Fludrocortisone | HO-CH$_2$-CO-C(R)OH- | 381 (5) | 403 (70) | 761 (0), 783 (0) |
| 9 | Reserpine | -NH-, -CO-O- | 609 (1) | | |
| 10 | Cyclosporin A | -CO-CHR-NH-CO-CHR-NR-CO-CHR-NH- | 602$^{2+}$ (0) 1203+ (0) | 613$^{2+}$ (0) 1225+ (0) | 621 (0), 633 (0),1220 (0) |
| 11 | Omeprazole | -SO-, -N=C-NH- | 346 (25) | | |
| 12 | OH-omeprazole | -SO-, -N=C-NH-, -OH? | 362 (8) | | 344 (0), 346 (2), 376 (2) |
| 13 | Clonazepam | benzodiazepine, Ph-NO$_2$, -NH-CO-CH(OH)-N=CR- | 316 (2) | 338 (70) | |
| 14 | Lorazepam | -NH-CO-CH(OH)-N=CR-, benzodiazepine | 321 (0) | | |
| 15 | Diazepam | -NCH$_3$-CO-CH$_2$-N=CR-, benzodiazepine | 285 (1) | | |

Figure 19

Table 2/3

| # | Compound name | Functional groups, or possible reaction sites | [M+H]+ (%) reactive | [M+Na]+ (%) reactive | Others [ ]+ (%) reactive |
|---|---|---|---|---|---|
| 16 | Prazepam | -NCH$_2$(cyclo-C$_3$H$_5$)-CO-CH$_2$-N=CR- | 325 (1) | | |
| 17 | - | | 271 (0) | | |
| 18 | Flunitrazepam | -NH-CO-CH$_2$-N=CR-, benzodiazepine | 314 (1) | 336 (75) | 268 (-) |
| 19 | Simazine | triazine (cyclic-C$_3$N$_3$), -NH-R | 202 (<u>75</u>) | | |
| 20 | - | triazine (cyclic-C$_3$N$_3$), -NH-R, -OH | 184 (1) | | |
| 21 | Terbutylazine | triazine (cyclic-C$_3$N$_3$), -NH-R | 230 (2) | | |
| 22 | - | triazine (cyclic-C$_3$N$_3$), -NH-R, -NH$_2$ | 174 (10) | | |
| 23 | Thiamine HCl (V-B1) | pyrimidine, thiazole, -NH$_2$, -OH | 265 (3) | | 109 (-) |
| 24 | Hemineurine | thiazole, -NH$_2$, -OH | 144 (0) | | |
| 25 | - | | 122 (80) | | |
| 26 | Nicotinic acid (a B3) | pyridine, -COOH | 124 (20) | | |
| 27 | Nicotinamide (a B3) | pyridine, -CO-NH$_2$ | 123 (10) | | |
| 28 | Angiotensin I | Asp-Arg-Val-Tyr-Ile-His-Pro-Phe-His-Leu [-COOH, -NH$_2$, HN=C(NH$_2$)-HN-, HO-C$_6$H$_4$-, 1H-imidazol] | 433$^{3+}$ (0) 649$^{2+}$ (0) 1297$^+$ (0) | | |
| 29 | Angiotensin II | Asp-Arg-Val-Tyr-Ile-His-Pro-Phe [-COOH, -NH$_2$, HN=C(NH$_2$)-HN-, HO-C$_6$H$_4$-, 1H-imidazol] | 524$^{2+}$ (0) 1046$^+$ (0) | | |
| 30 | Bradykinin | Arg-Pro-Pro-Gly-Phe-Ser-Pro-Phe-Arg HN=C(CH$_2$)-HN-, HO-CH$_2$-, HN=C(NH$_2$)-HN- | 531$^{2+}$ (0) | | |

Figure 20

Table 3/3

| # | Compound name | Functional groups, or possible reaction sites | [M+H]+ (%) reactive | [M+Na]+ (%) reactive | Others [ ]+ (%) reactive |
|---|---|---|---|---|---|
| 31 | Paroxetine | $R_2NH$, 1,3-dioxole | 330  (3) | | |
| 32 | - | | 192  (2) | | |
| 33 | Imipramine | $R_3N$ | 281  (0) | | |
| 34 | - | | 86  (0) | | |
| 35 | Midazolam | benzodiazepine | 326  (0) | | |
| 36 | Verapamil (base) | $CH_3O-$, $-CN$, $R_3N$ | 455  (0) | 477  (0) | |
| 37 | - | $CH_3O-$, $-CN$, $R_3N$ | 303  (0) | | |
| 38 | - | $CH_3O-$ | 165  (20) | | |
| 39 | Theophylline | 1H-imidazol, pyrimidine, | [181]+ (15) | [203]+ (65) [383]+ (40, dissoc.) | [2M+H]+ (65, dissoc.) |
| 40 | Estrone | phenol, carbonyl, -OH | [271]+ (2) | | [288]+ (15, disso.) |
| 41 | - | | [253]+ (0) | | |

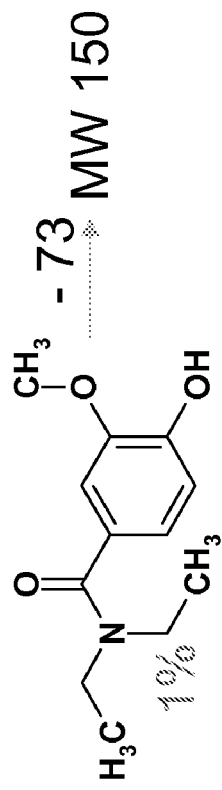
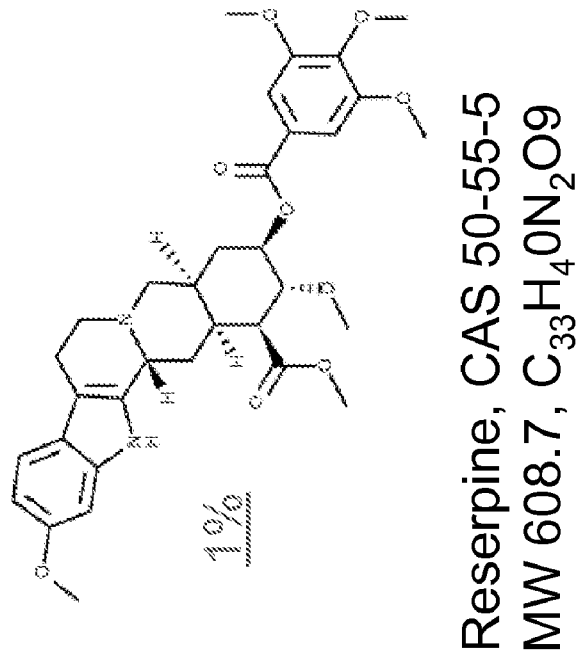
Etamivan, MW 223.27, CAS 304-84-7
Reserpine, CAS 50-55-5
MW 608.7, $C_{33}H_{40}N_2O_9$
Figure 31
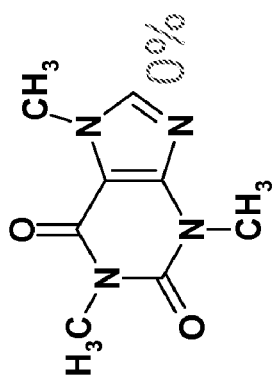
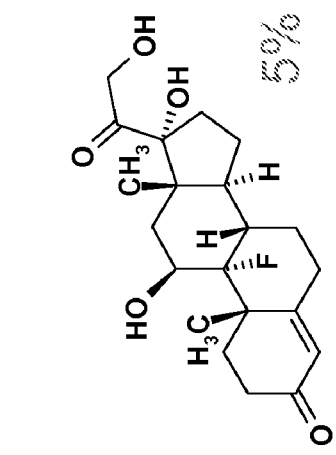
Caffeine, MW 194.19, CAS 58-08-2
Fludrocortisone, CAS 127-31-1
MW 380.2, $C_{21}H_{29}O_5F$

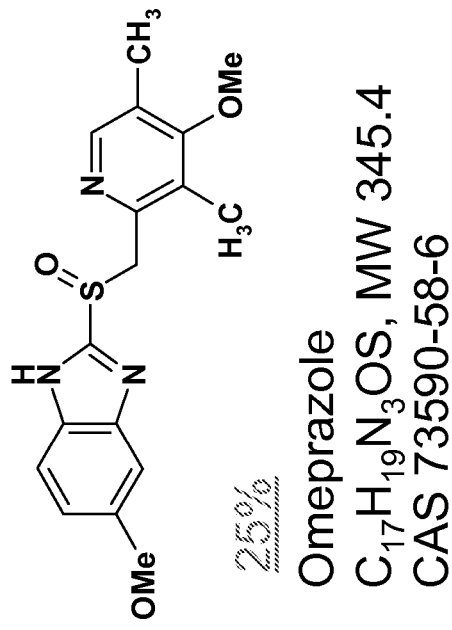
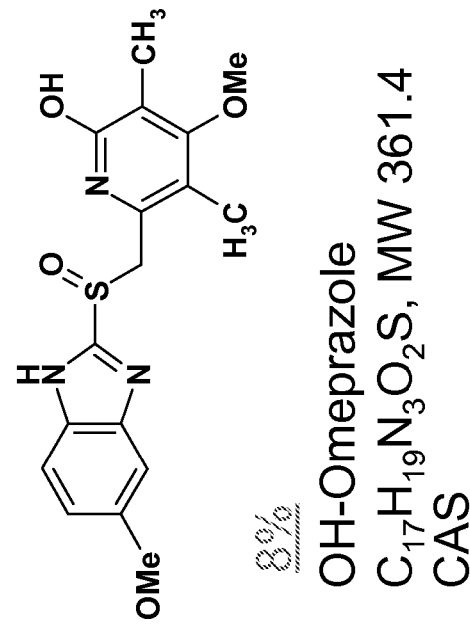
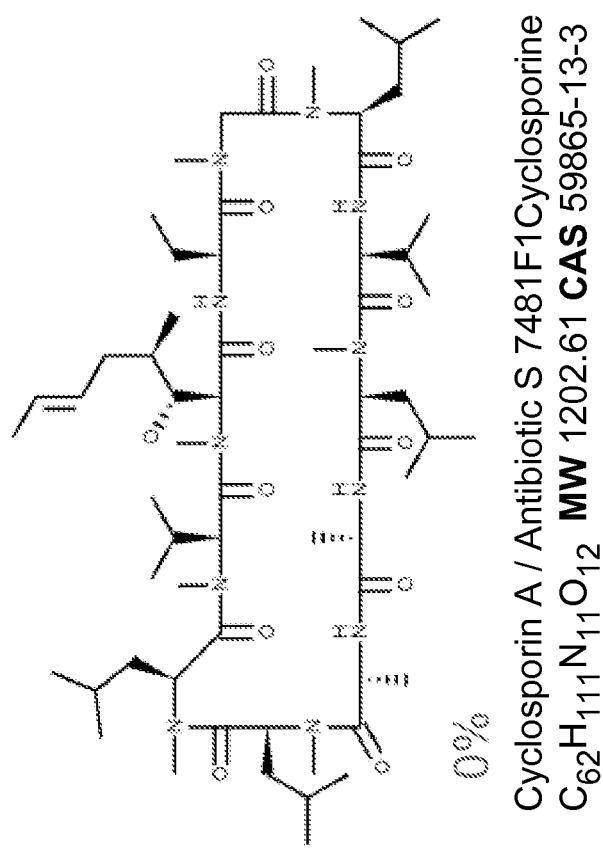
Figure 32

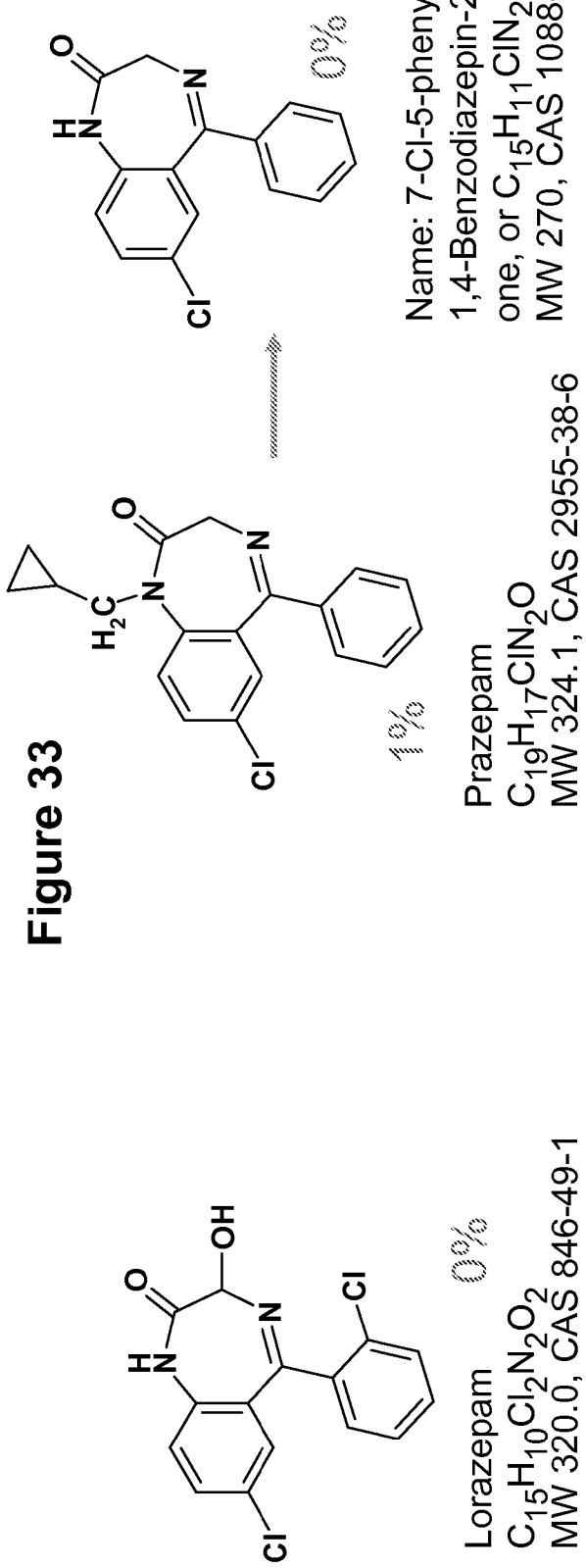
Figure 33

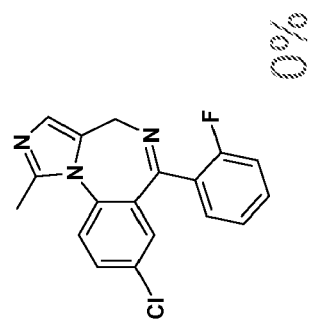
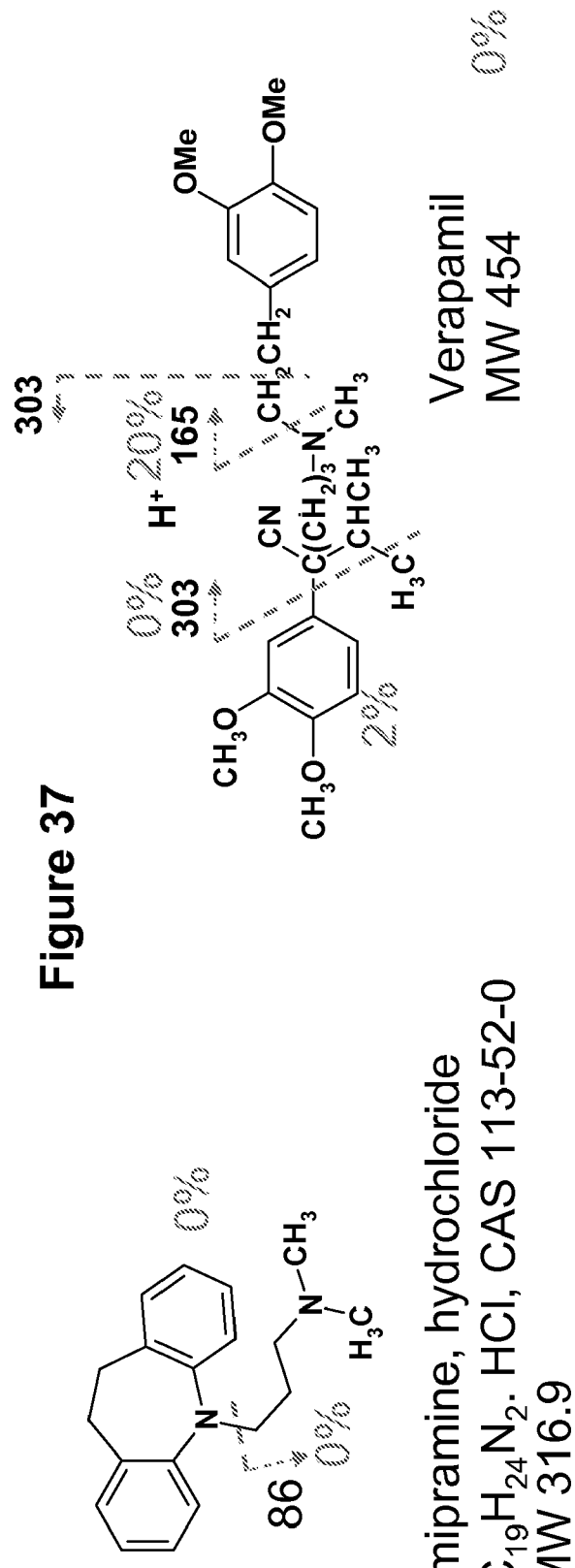
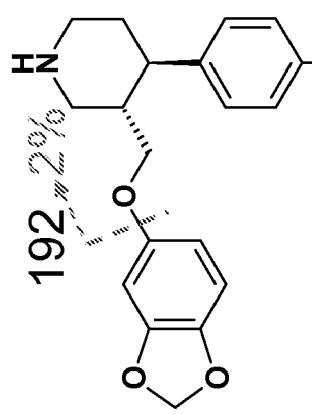
Figure 37

CHEMICAL NOISE REDUCTION FOR MASS SPECTROMETRY

CROSS-REFERENCE TO RELATED APPLICATIONS

The present application claims the benefit of and priority to copending U.S. provisional application No. 60/765,809 filed Feb. 7, 2006, the entire contents of which are herein incorporated by reference.

INTRODUCTION

The interference of background ions (chemical noise) has been a problem since the inception of mass spectrometry. This is most acute when analytes with a low concentration, low ionization efficiency, or both, are studied. Chemical noise can arise in a variety of mass spectrometry ion sources such as, for example, an electrospray ionization (ESI), matrix-assisted laser desorption ionization (MALDI), atmospheric pressure chemical ionization (APCI), and atmospheric pressure photoionization (APPI) sources. For example, ESI ion sources can serve as a means for introducing an ionized sample that originates from a LC column into a mass separator apparatus. Attempts have been made to reduce chemical noise in HPLC-MS using either hardware or software approaches, however, chemical noise can remain even when an improved interface for de-clustering and high purity HPLC solvents are used.

MALDI spectra, in particular in the low mass region of the spectra where small molecule molecular ions reside, are often dominated by chemical noise to a much greater extent than ESI spectra. It is believed that the majority of this chemical noise is due to matrix molecules. The problem can be so great as to preclude the use of systems using MALDI ion sources from qualitative small molecule analytical applications. Over the past several years, the scientific community has directed great effort at solving this problem by attempting to develope matrixless MALDI surfaces. However, the matrixless approach can result in both a loss of sensitivity and lead to irreproducibility compared to conventional matrix systems which transfer the laser energy via the matrix to ionize analytes.

SUMMARY

This present teachings provide various methods that use a neutral chemical reagent and one or more mass filters to reduce interfering chemical background ion signals that are generated by ionization sources of mass spectrometers. In various embodiments, the neutral chemical reagent belongs to the class of organic chemical species containing a disulfide functionality.

In various aspects, the present teachings present a novel mass spectrometric approach to reduce the chemical interference in LC-MS, which can be realized by reactions between chemical background ions and a chemical reagent combined with an arrangement of band-pass filters based on ion mobility, mass-to-charge ratio, or both, e.g., an arrangement using a mass scanning/filtering function of quadrupoles. This technique has been implemented on a standard triple quadrupole LC-MS, and can be optimized on a dedicated LC-MS instrumentation.

We have discovered that a chosen chemical reagent, such as dimethyl disulfide and ethylene oxide, etc., react substantially exclusively with the major chemical background ions rather than with the protonated analytes (for example, small molecule pharmaceuticals and peptides) in LC/MS. It is believed, without being held to theory, that this is most likely due to the difference in structures between most chemical background ions and conventional protonated molecules. Chemical background ions are mainly classified as either cluster-related ions or stable ions of (degraded) contaminants (airborne or from the tubing and solvents).

The reactions are efficient and can fit well with the pressure encountered in the ion source, mass analyzer, or both, and can match the scan speed of a quadrupole MS. While combined with the zero neutral loss scan mode of a triple quadrupole LC-MS, the exclusive reactions can be applied, for example, to selectively reduce the level of chemical background noise and improve the signal-to-noise ratio in the LC/MS of organic analytes. The present teachings present examples of tests on a variety of types of analyte ions, which indicate a generic and practical application of the techniques of the present teachings. In various embodiments, a reduction of baseline noise in LC/MS by a factor of 10-30 and an improvement of signal-to-noise ratio 5-10 times can be achieved. The noise reduction thus afforded could be useful for both quantitative and qualitative analyses, small molecule applications of all types as well as large molecule proteomic applications.

The chemical noise reduction methods of the present teachings can be used with a variety of mass spectrometry and ion mobility systems and analytical techniques. Mass spectrometry systems to which various embodiments of the present teachings can be applied include, but are not limited to, those comprising two mass separators with a collision cell disposed in the ion flight path between the two mass separators, those comprising two ion mobility mass separators with a collision cell disposed in the ion flight path between them; and combinations of a mass separator and an ion mobility separator with a collision cell disposed in the ion flight path between them. In various embodiments, a single mass separator or ion mobility separator can be used where reactions with the chemical reagent are confined towards the exit portion of the separator.

Examples of suitable mass separators include, but are not limited to, quadrupoles, RF multipoles, ion traps, time-of-flight (TOF), and TOF in conjunction with a timed ion selector. Examples of suitable ion mobility separators include, but are not limited to, differential ion mobility spectrometers analyzers (DMS) also referred to as high field asymmetric waveform ion mobility spectrometers (FAIMS), and substantially symmetric field ion mobility spectrometers (IMS), all of which can be used in conjunction with a timed ion selector to provide, e.g., an ion filtering function. The present teachings can be applied, in various embodiments, to reduce chemical noise originating from a variety of ion sources including, but not limited to, an electrospray ionization (ESI), matrix-assisted laser desorption ionization (MALDI), surface-enhanced laser desorption ionization (SELDI), atmospheric pressure chemical ionization (APCI), and atmospheric pressure photoionization (APPI) sources.

Examples of mass spectrometry systems to which various embodiments of the present teachings can be applied include, but are not limited to, those which comprise one or more of a triple quadrupole, a quadrupole-linear ion trap (e.g., 4000 Q TRAP® LC/MS/MS System, Q TRAP® LC/MS/MS System), an LC/MS/MS system (API 5000®, API 4000®, API 3000®, API 2000®, etc.), a quadrupole TOF (e.g., QSTAR® LC/MS/MS System), and a TOF-TOF. Examples of mass spectrometry analytical techniques to which various embodiments of the present teachings can be applied include, but are not limited to, various forms of parent-daughter ion transition monitoring (PDITM) such as, for example, what are referred to as selective ion monitoring (SIM) and multiple reaction monitoring (MRM) techniques.

In various embodiments of the teachings described herein, the neutral chemical reagent can be applied to substantially selectively reduce the level of chemical background noise and improve the signal-to-noise ratio in mass spectrometry of organic analytes. In various embodiments, this approach can be implemented on a triple quadrupole mass spectrometer by addition of the chemical reagent to the collision cell and operating the mass spectrometer in the zero neutral loss scan mode. Various embodiments of such operation are illustrated schematically in FIG. 1. In various embodiments, implementation of this noise reduction method can be achieved by adding the chemical reagent to a reaction region where an arrangement of a low mass filter prior to the reaction region (e.g., a filter that excludes ions below a selected mass-to-charge ratio value (m/z) from entering the reaction region), and a low and high mass filter after the reaction cell (e.g., a band pass filter that passes ions with an m/z value in a selected range of m/z values). In various embodiments, this approach can be implemented on a ion mobility based spectrometer, e.g., comprising two ion mobility separators (e.g., an DMS and IMS, two IMS, two DMS, etc.) with a collision cell between them.

Various embodiments of such arrangements, for example, use of a bandpass mass filter after the reaction cell in the optics region of the vacuum chamber prior to the mass analyzer, are illustrated schematically in FIGS. 2A-2C and 3A-3C. In various embodiments, such filters could be constructed from one or more high-field assymetric waveform ion mobility spectrometry (FAIMS) devices located in the atmospheric ion source region, see, for example, FIG. 3C. The flexibility of such an arrangement can provide, for example, a triple quadrupole instrument to benefit from a chemical noise reduction method of the present teachings when operating in all scan modes. In various embodiments, can also provide for implementation of the present teachings on other types of mass spectrometers including, but limited to, TOF, linear and 3-D traps, Fourier transform mass spectrometers (FTMS), orbit traps, and magnetic sector instrumentations. For example, in various embodiments, the use of a chemical reagent and a band pass mass filter prior to the mass analyzer, could be used as a means to reduce the space charge effects on ion trapping type mass analyzers as well as to reduce chemical noise in these instrumentations.

In various embodiments, the reduction of chemical noise facilitated by the present teachings can be useful for both quantitative and qualitative analyses, small molecule applications of all types as well as large molecule proteomic applications.

Various embodiments of the present teachings can facilitate improving signal/noise in both quantitative and qualitative applications of mass spetrometry. In various embodiments, the present teaching can be used in combination with other techniques for chemical noise reduction. For example, because the present teachings can reduce chemical noise before detection occurs, in various situations the present teachings can provide additive improvements to software methods such as, e.g., dynamic background subtraction, and other data processing methods currently in use. In various embodiments, the present teachings can be used in situations where LC is not used as a means of sample introduction (e.g., nanoESI infusion type methods) where, for example, background subtraction methods do not work because there are no analyte free regions in the data from which to derive a background spectra.

In various aspects, the present teachings provide articles of manufacture where the functionality of a method of the present teachings is embedded as computer-readable instructions on a computer-readable medium, such as, but not limited to, a floppy disk, a hard disk, an optical disk, a magnetic tape, a PROM, an EPROM, CD-ROM, or DVD-ROM.

The forgoing and other aspects, embodiments, and features of the teachings can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the teachings.

BRIEF DESCRIPTIONS OF THE DRAWINGS

FIG. 1 schematically depicts a triple quadrupole equipped with a chemical reagent gas (reaction gas) inlet to the collision cell (reaction cell).

FIGS. 2A-C schematically depict various embodiments of band pass filter arrangements prior to the mass analyzer. Where FIG. 2A schematically depicts a low resolution quadrupole based filters that can simulate a zero neutral loss experiment in the Q0 region of the mass spectrometer of FIG. 1, and having separate high pressure cells for pre-reaction filtering (high pass filter), reaction, and post-reaction filtering (band pass filtering); where FIG. 2B schematically depicts an arrangement similar to FIG. 2A but combining the post-reaction filter and the reaction cell; and where FIG. 2C schematically depicts an arrangement where Q0 serves as pre-reaction high pass filter, the reaction cell is in millitorr Q0 region, and Q1 serves as post-reaction band pass filter.

FIGS. 3A-C schematically depict various embodiments of band pass filter arrangements prior to the mass analyzer. Where FIG. 3A schematically depicts Q0 serving as a pre-reaction high pass filter and reaction gas (neutral chemical reagent) is added to the entrance of Q1 where reactions and post-reaction filtering occurs; where FIG. 3B schematically depicts an arrangement where Q1 serves as both pre and post-reaction filter and reaction gas (neutral chemical reagent) is added to the middle of the quadrupole in a fashion where reactions do not substantially occur in the front, high pass filter region; and where FIG. 3C schematically depicts an arrangement where ion mobility filters are in the atmospheric ion source region based on FAIMS mobility and with addition of the chemical reagent gas to the drift gas in the middle of a FAIMS cell wherein the front portion of the reaction cell would filter pre-reaction and the back half of the reaction cell would filter post-reaction. It is to be understood that the FAIMS cell can comprise multiple FAIMS regions with reaction gas added to one or more of these regions. Multiple FIAMS cells can facilitate, for example, the use of one or more different drift gases, drift voltages, and combinations thereof.

FIGS. 4A-4B depict examples of ESI background reduction when using DMDS in the collision cell in zero neutral loss (ZNL) mode is compared to using nitrogen but no DMDS in the collision cell. FIG. 4A depicting mass spectra without DMDS reaction gas and FIG. 4B mass spectra with the addition of DMDS to the collision cell. The reactions occur with an estimated 95% of the total chemical background ions from this LC/MS mobile phase and others tested with electrospray ionization.

FIG. 5 depicts the effect on the total ion current (TIC) when DMDS is applied and ZNL scanning where regions correspond to the following: (a) DMDS added to cell; (b) no gas added to cell; and (c) only nitrogen added to the cell.

FIGS. 6A and 6B depict, respectively, mass spectra under the conditions of regions (a) and (c) of FIG. 5.

FIGS. 7A-7B compare ZNL mass spectra of Prazepam, a high proton affinity compound, with (FIG. 7B) and without DMDS (FIG. 7A) added to the collision cell. Background is reduced and molecular ion remains substantially unattenuated.

Figure 8:
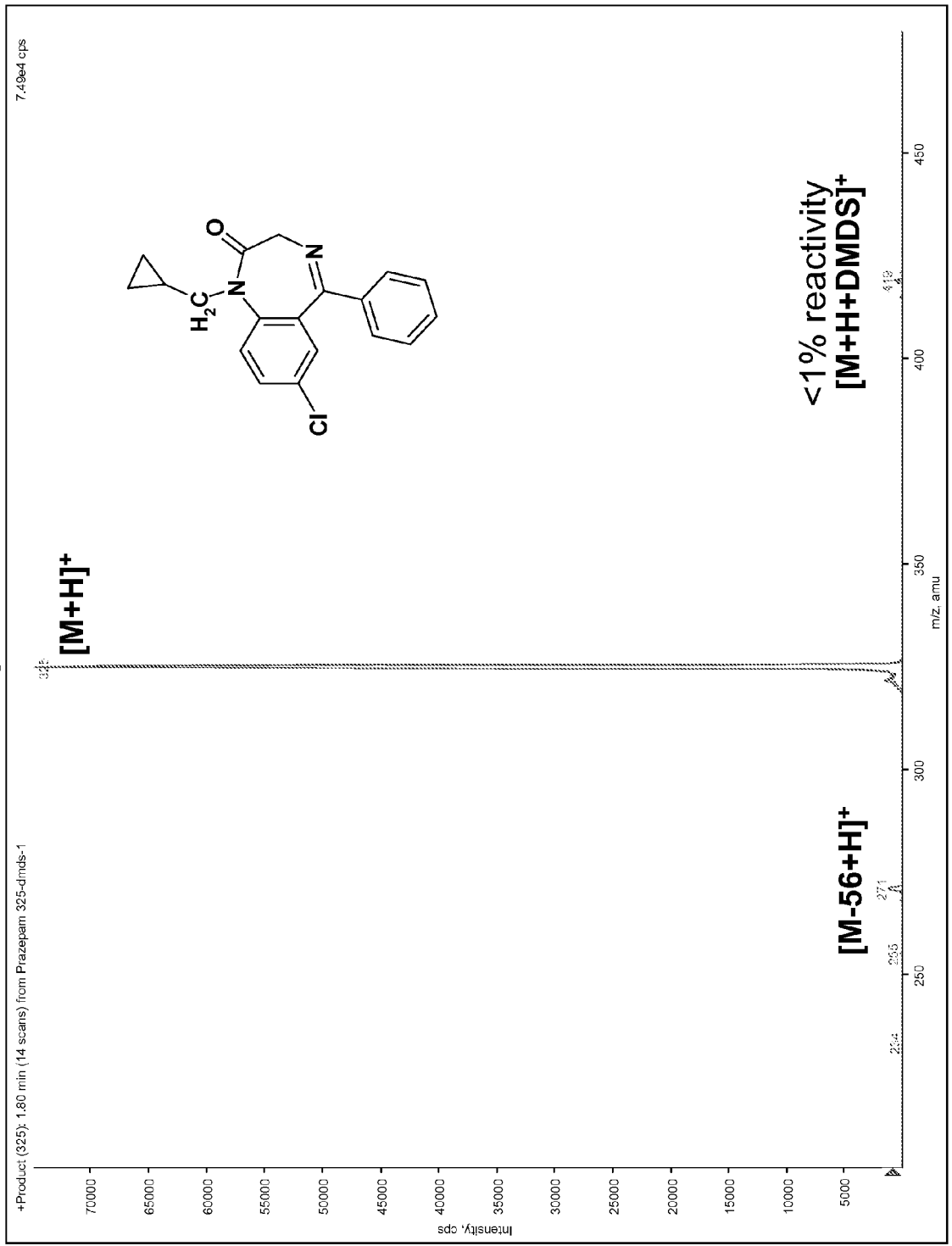

FIG. 8 depicts mass spectral data used to ascertain the extent of reaction of DMDS with Prazepam; reactivity of DMDS with Prazepam was observed to be less than about 1%.

FIGS. 9A-9C present data on Midazolam. FIGS. 9A-9B compare ZNL mass spectra of Midazolam, a high proton affinity compound, with (FIG. 9B) and without DMDS (FIG. 9A) added to the collision cell. Background is reduced and molecular ion remains substantially unattenuated. FIG. 9C (inset in FIG. 9B) shows a product ion spectrum demonstrating that there is substantially no reaction of Midazolam with DMDS.

FIGS. 10A-10B compare ZNL mass spectra of Fludrocortisone, a low proton affinity compound, with (FIG. 10B) and without DMDS (FIG. 10A) added to the collision cell.

Figures 11A, 11B:
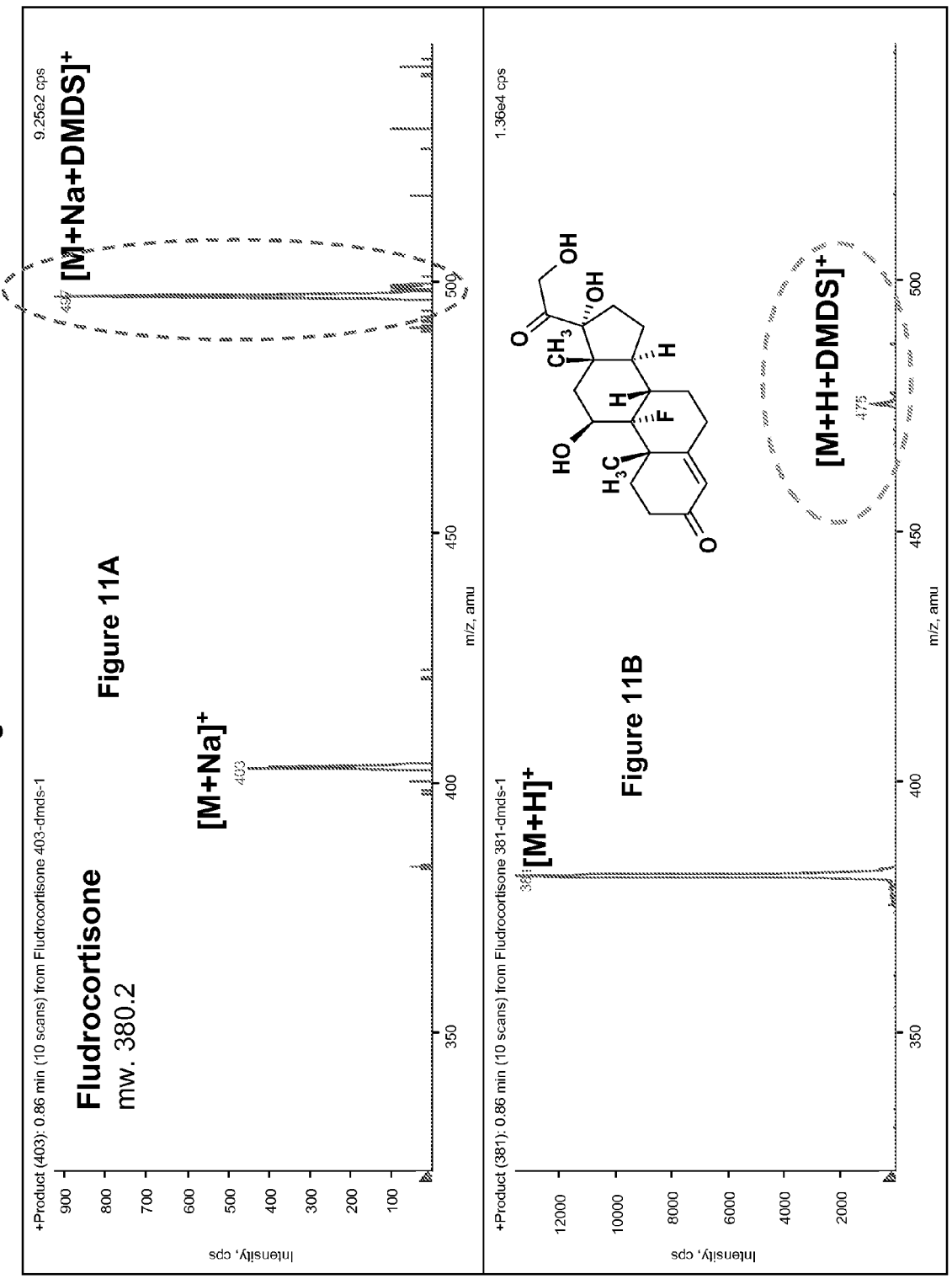

FIGS. 11A-11B assess reactions of Fludrocortisone with DMDS using the product ion scan method; FIG. 11A presenting data on sodiated Fludrocortisone reaction with DMDS and FIG. 11B data on protonated Fludrocortisone with DMDS.

FIGS. 12A-12B compare ZNL mass spectra of estrone, a relatively low proton affinity compound, with (FIG. 12B) and without DMDS (FIG. 12A).

FIGS. 13A-13B assess reactions of protonated and sodiated flunitrazepam with DMDS using product ion scanning.

FIGS. 14A-14B assess reactions of Etamivan with DMDS using product ion scanning.

FIGS. 15A-15B compare ZNL mass spectra of cyclosporine A, a relatively low proton affinity peptide (no basic residues) with DMDS (FIG. 15B) and without DMDS (FIG. 15A) added to the collision cell.

FIGS. 16A-16D compare Angiotensin II background reduction with DMDS. FIGS. 16A (a) and 16B (b) compare a Q3 single MS scan (with N2 in the collision cell) with a zero neutral loss with nitrogen. This comparison shows that the ion current is reduced by about 2.5-3× by virtue of transmission losses to be expected when operating two RF/DC quadrupoles instead of one. FIG. 16C (c) and 16(d) compare the effect of DMDS at two different pressures.

Figure 17:
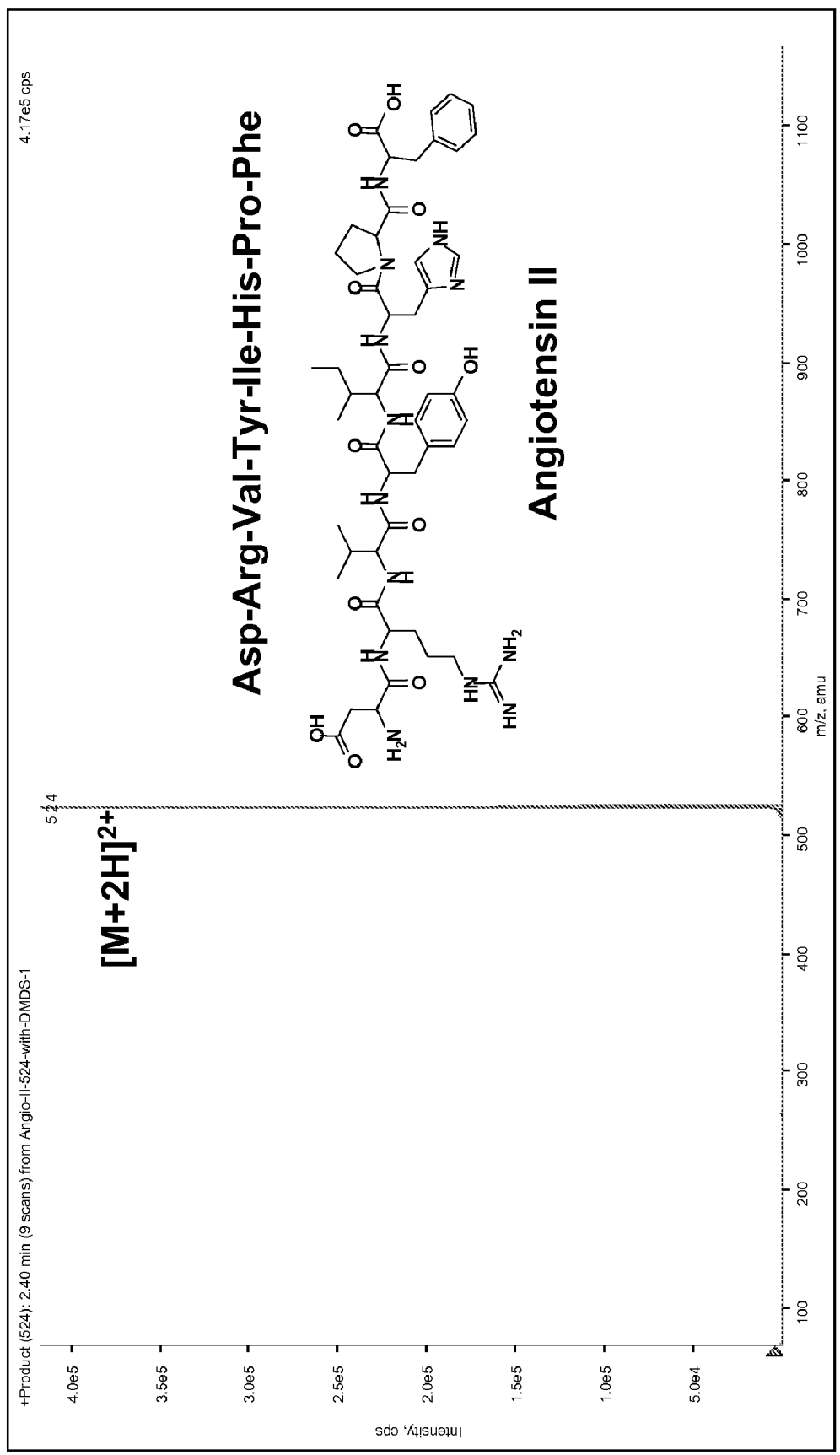

FIG. 17 depicts a product ion scan of the $[M+2H]^{2+}$ of Angiotensin II with DMDS in the cell at a 2 eV collision energy. FIGS. 18-20 are tables summarizing the extent of reaction of DMDS with a variety of compounds in the examples.

Figure 21:
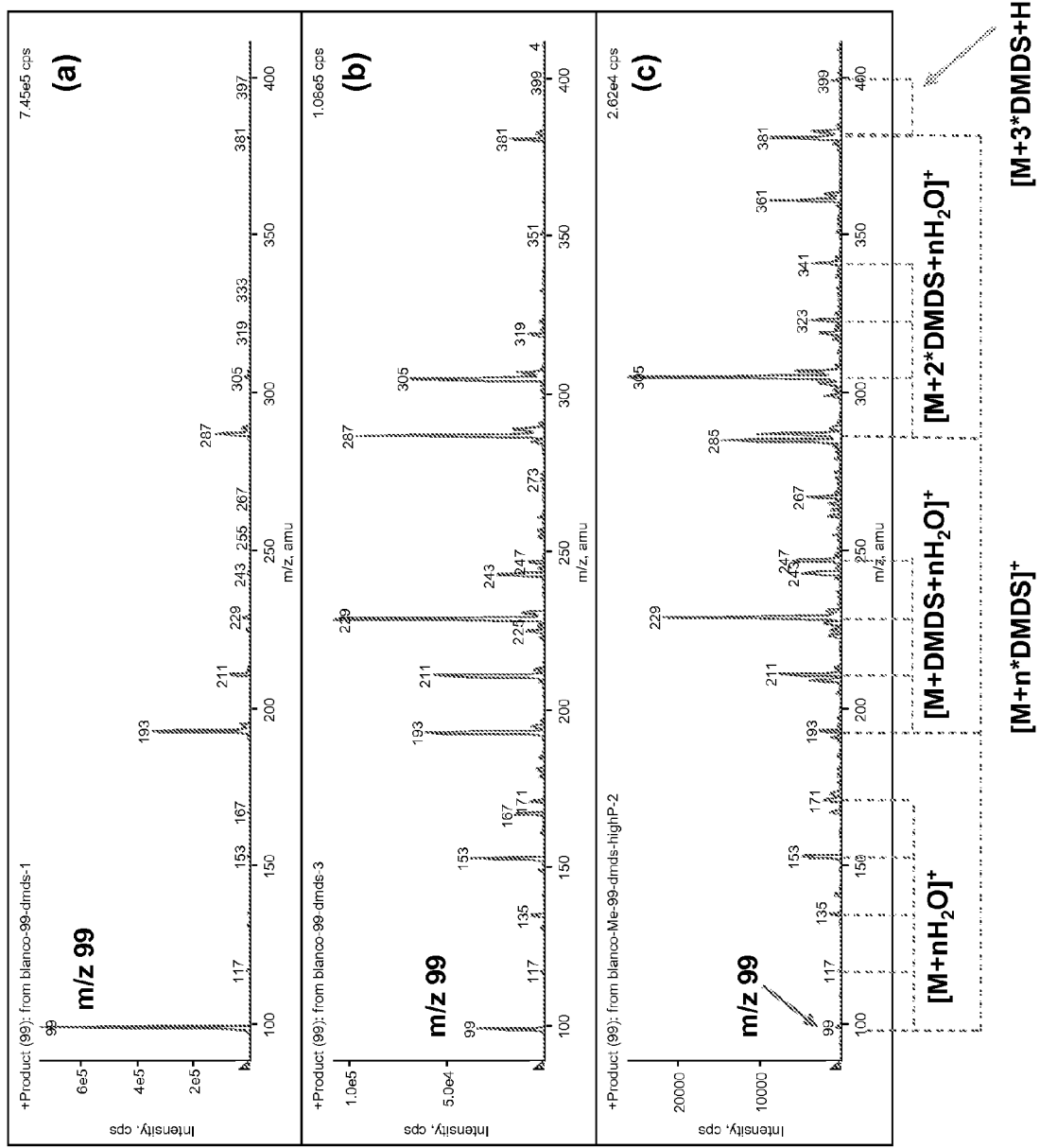
Figure 22:
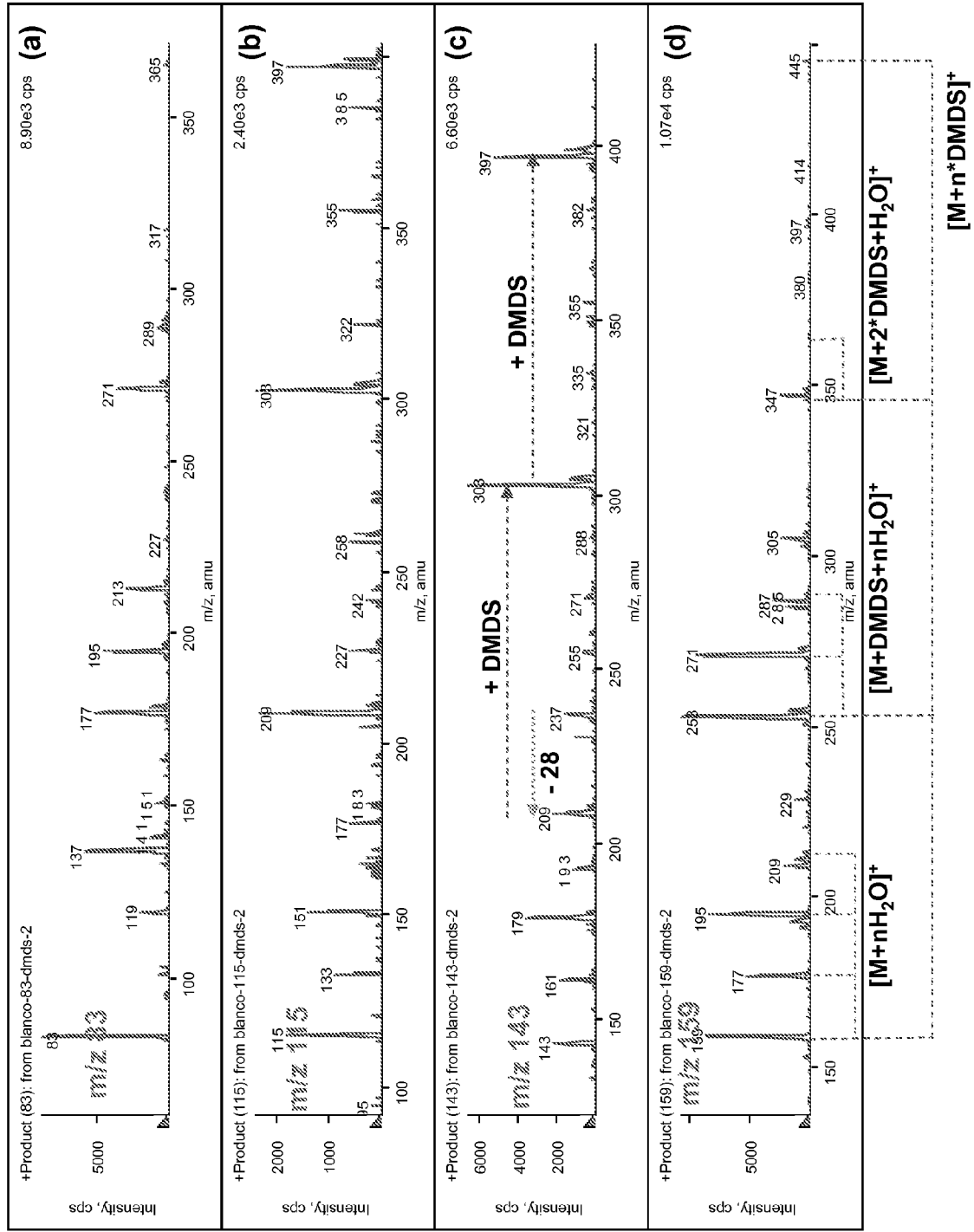
Figure 23:
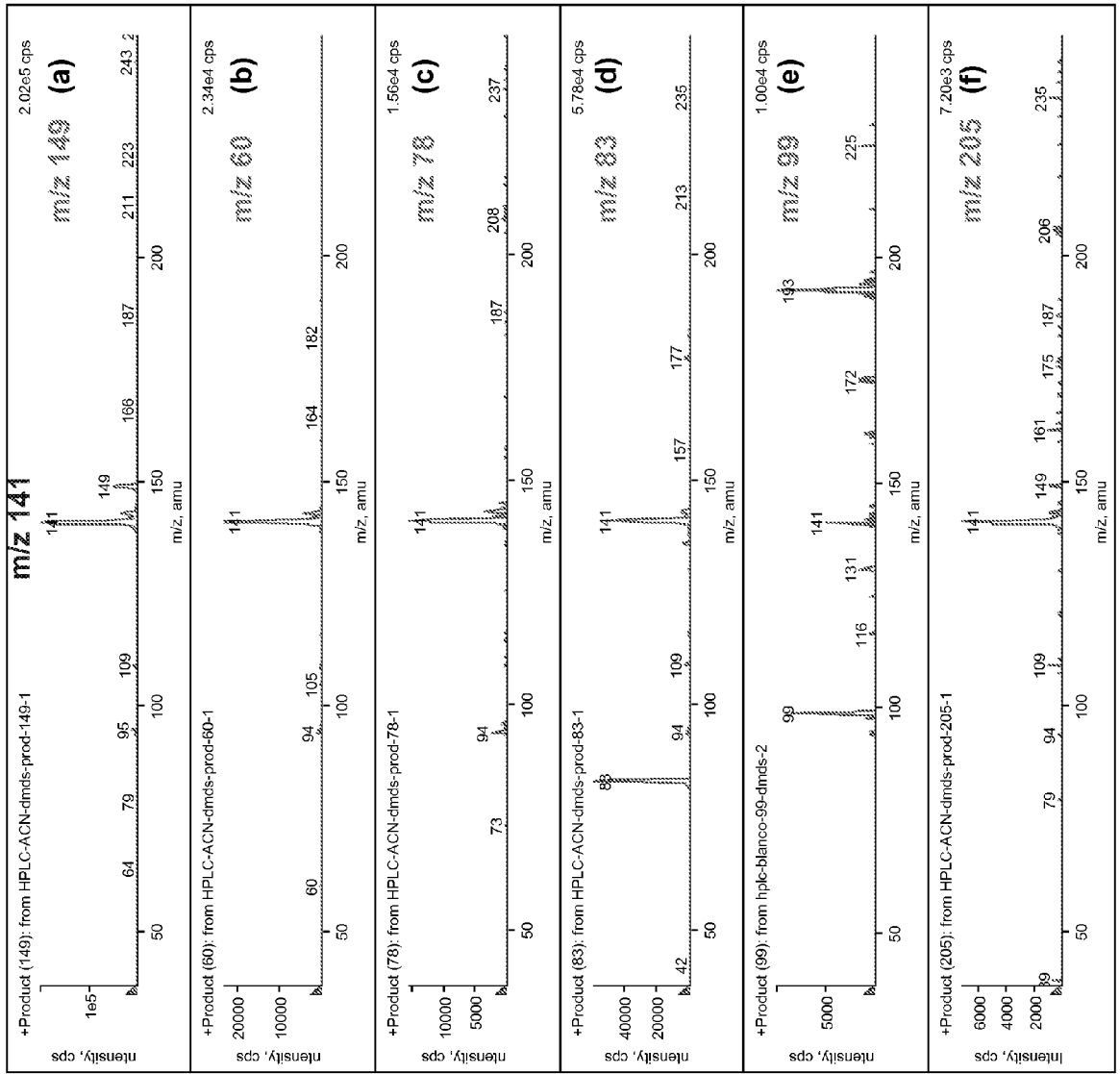

FIGS. 21A-21C assess the reactions of the background ion m/z 99 at different partial pressures of DMDS using product ion scanning above and below the mass of the targeted ion. Clusters of water and DMDS are observed. This m/z=99 ion was determined to be $P(OH)_4^+$ and is schematically illustrated, e.g., in FIG. 26.

FIGS. 22A-22D assess the reactions of four background ions as indicated in the figure header, m/z=83, m/z=115, m/z=143, and m/z=159, respectively.

FIGS. 23A-F assess the reactions of an additional six background ions which do not show extensive adduction but proceed by charge transfer. The spectra of FIGS. 23A-F are, respectively, the product ion scans of (a) m/z 149; (b) m/z 60; (c) m/z 78; (d) m/z 83; (e) m/z 99; and (f) m/z 205.

Figure 24:
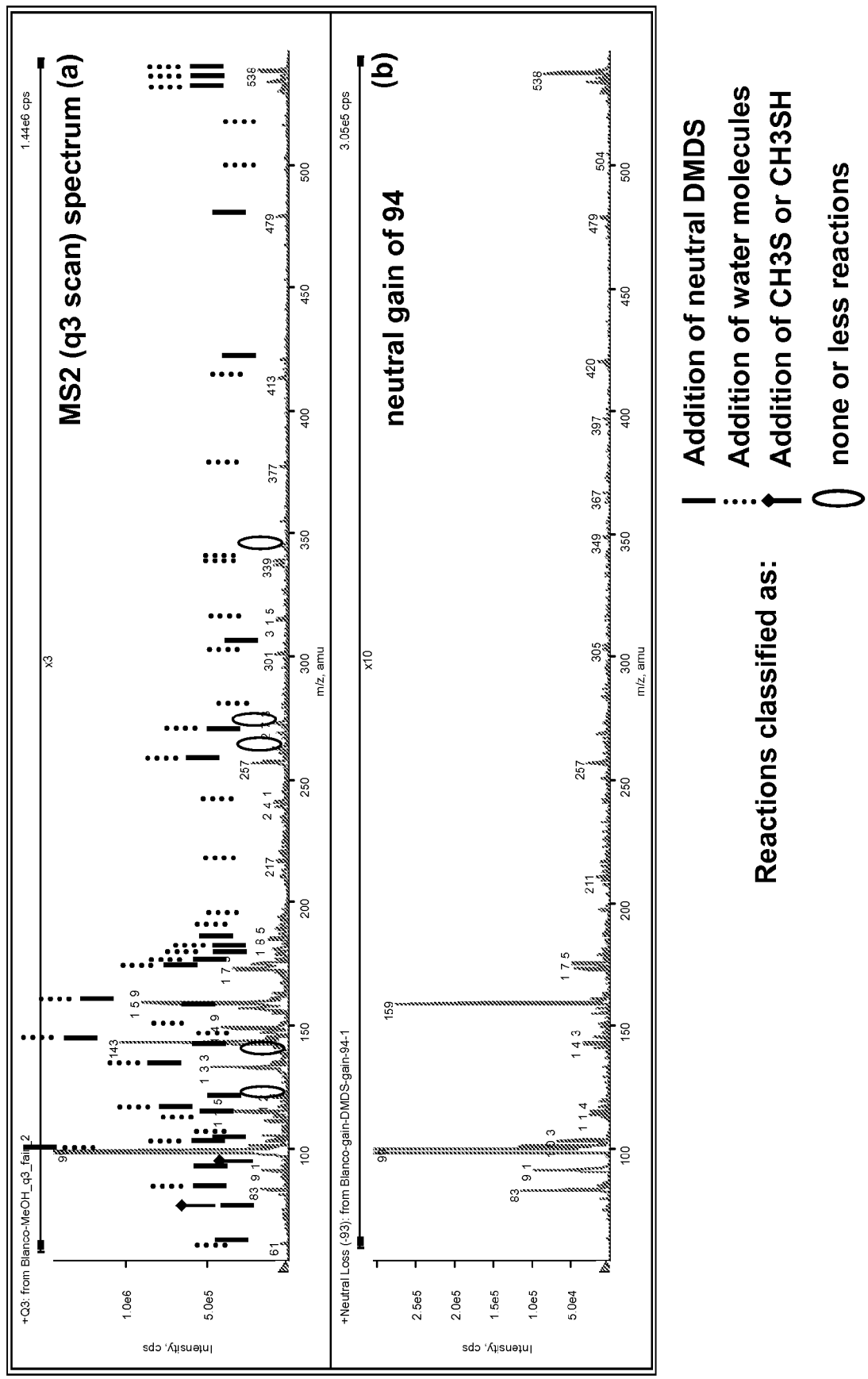

FIGS. 24A-B schematically depicts a summary of the reactivity and believed reaction channels of the background ions in a typical ESI spectrum of the examples with DMDS. A few of the background ions showed substantially no reactivity (circled ions).

Figure 25:
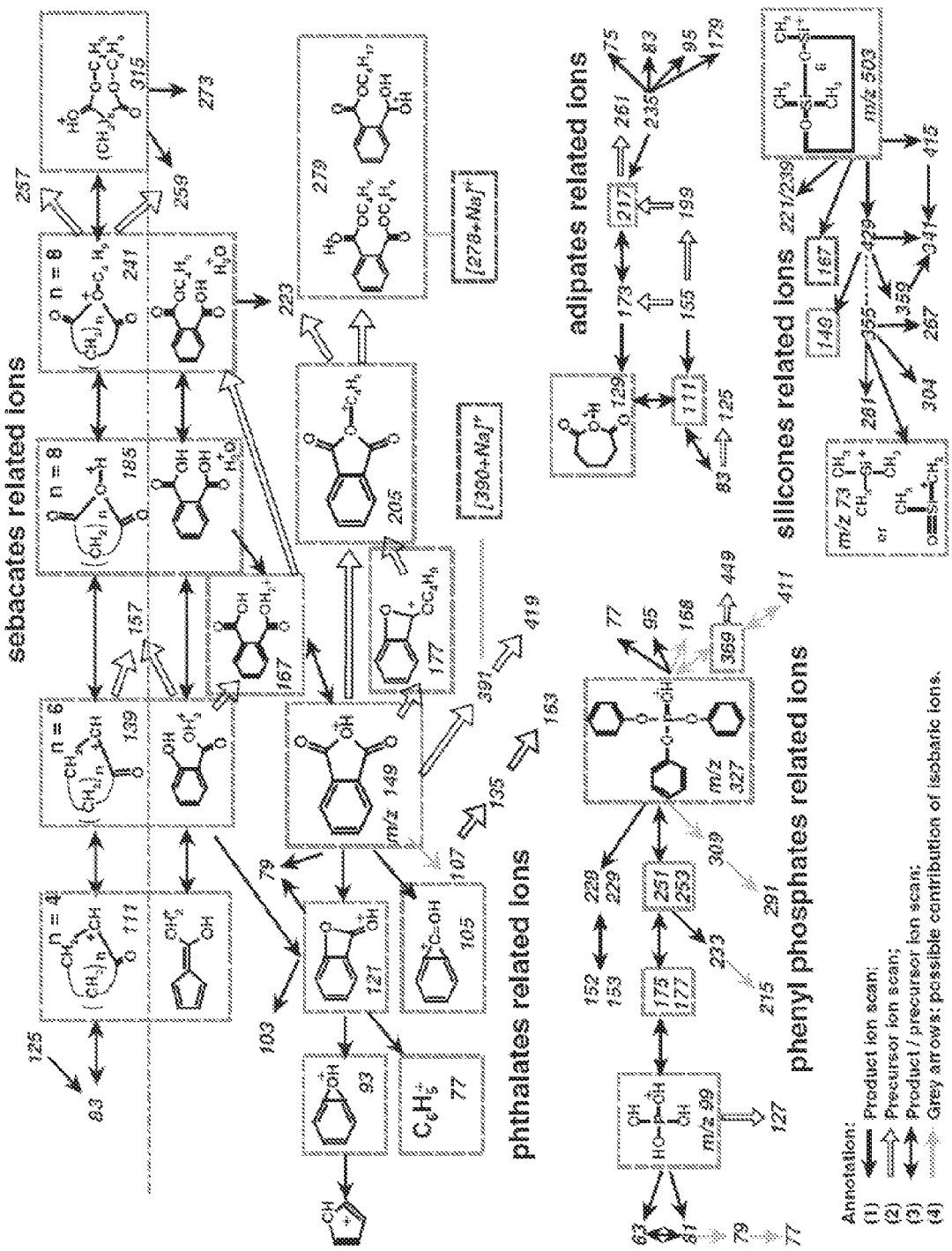
Figure 26:
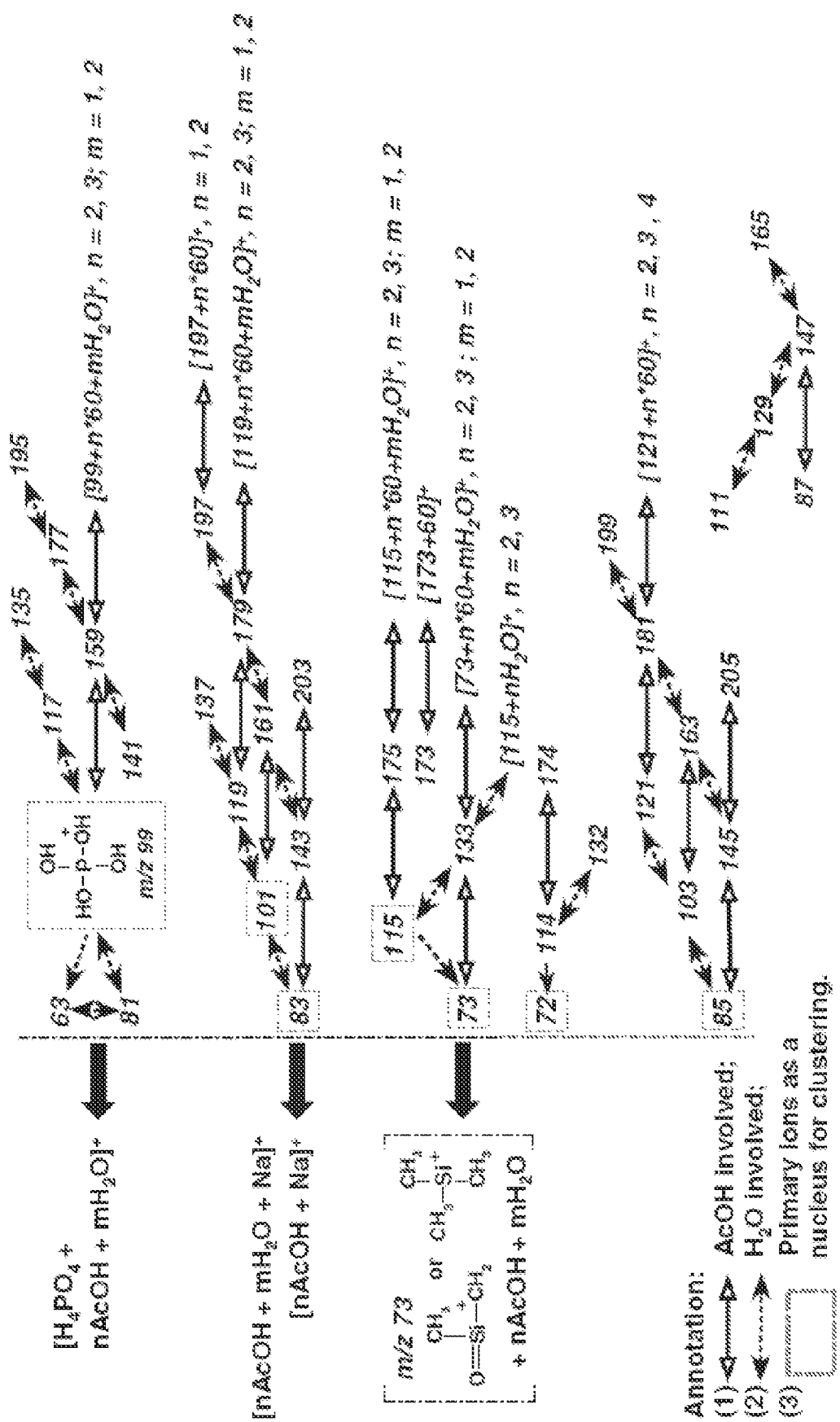

FIGS. 25 and 26 schematically summarize a study undertaken to identify common background ions using various MS/MS scan modes to establish the relationships among the ion populations.

Figure 27:
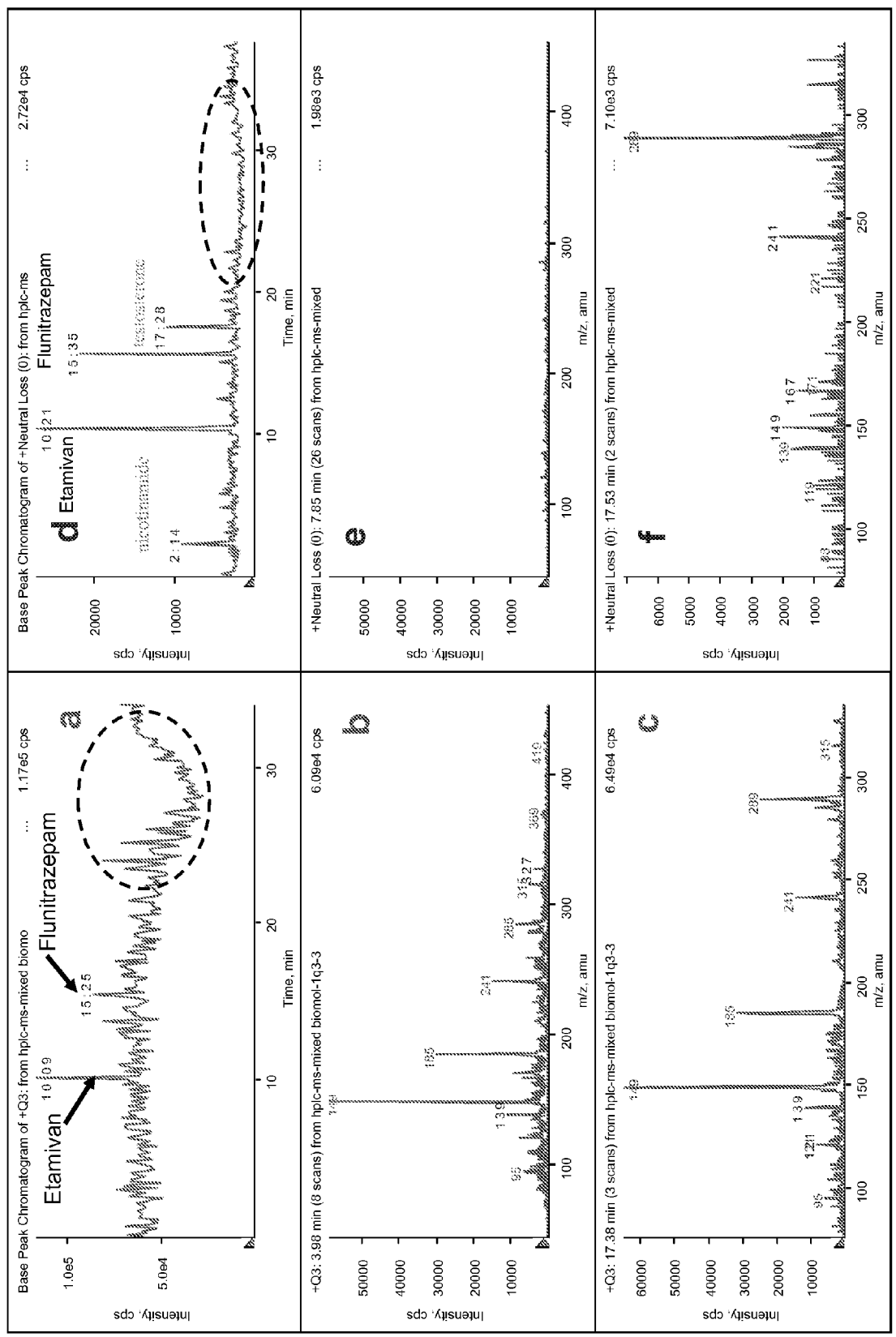

FIGS. 27A-27F depict TurboIon Spray LC/MS chromatograms and mass spectra of four pharmaceutical compounds, at 200 µL/min, nicotinamide, Etamivan, Flunitrazepam, and testosterone, without DMDS (FIGS. 27A, 27B and 27C) and with DMDS (FIGS. 27D, 27E and 27F).

Figure 28:
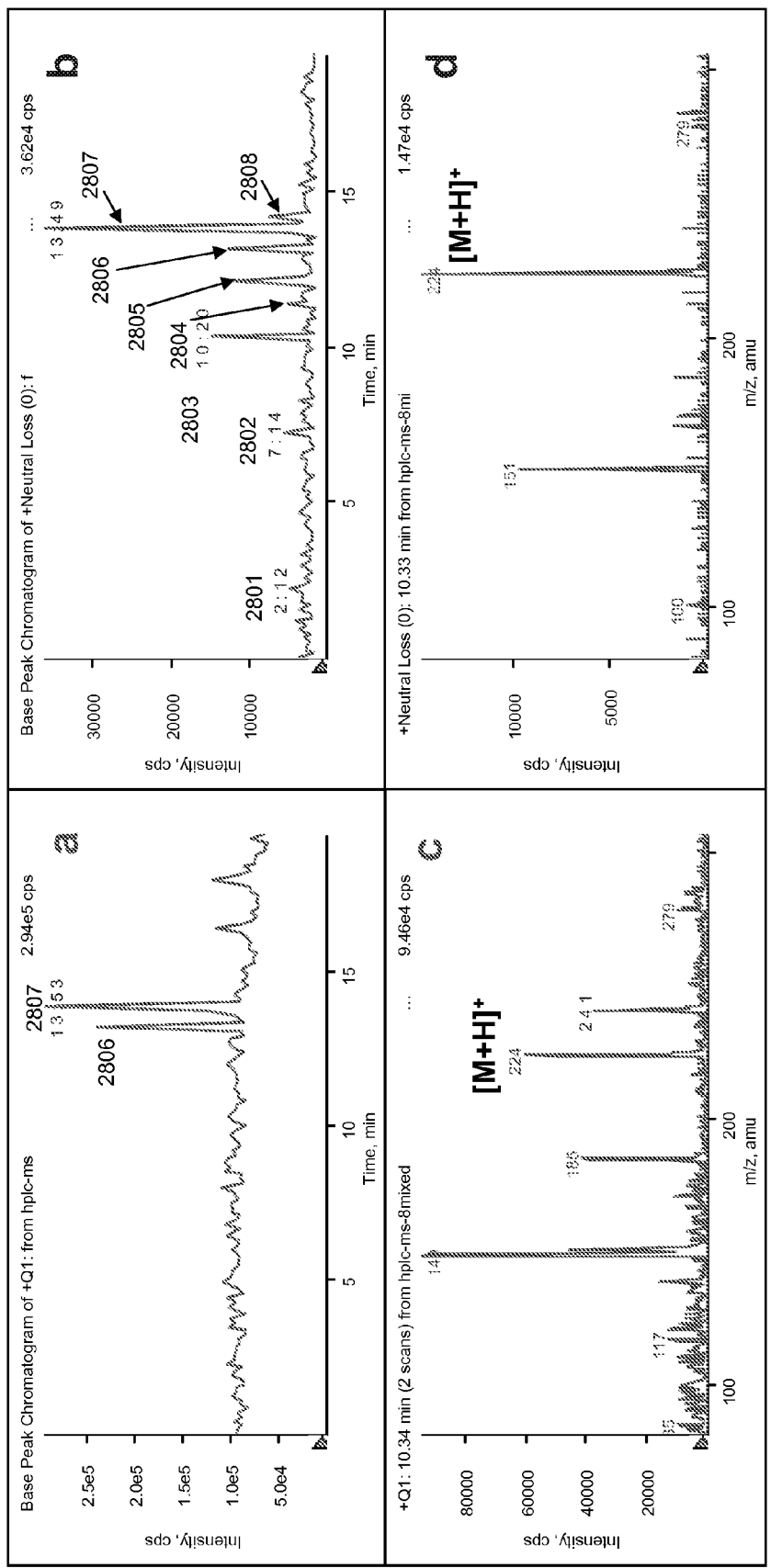
Figure 29:
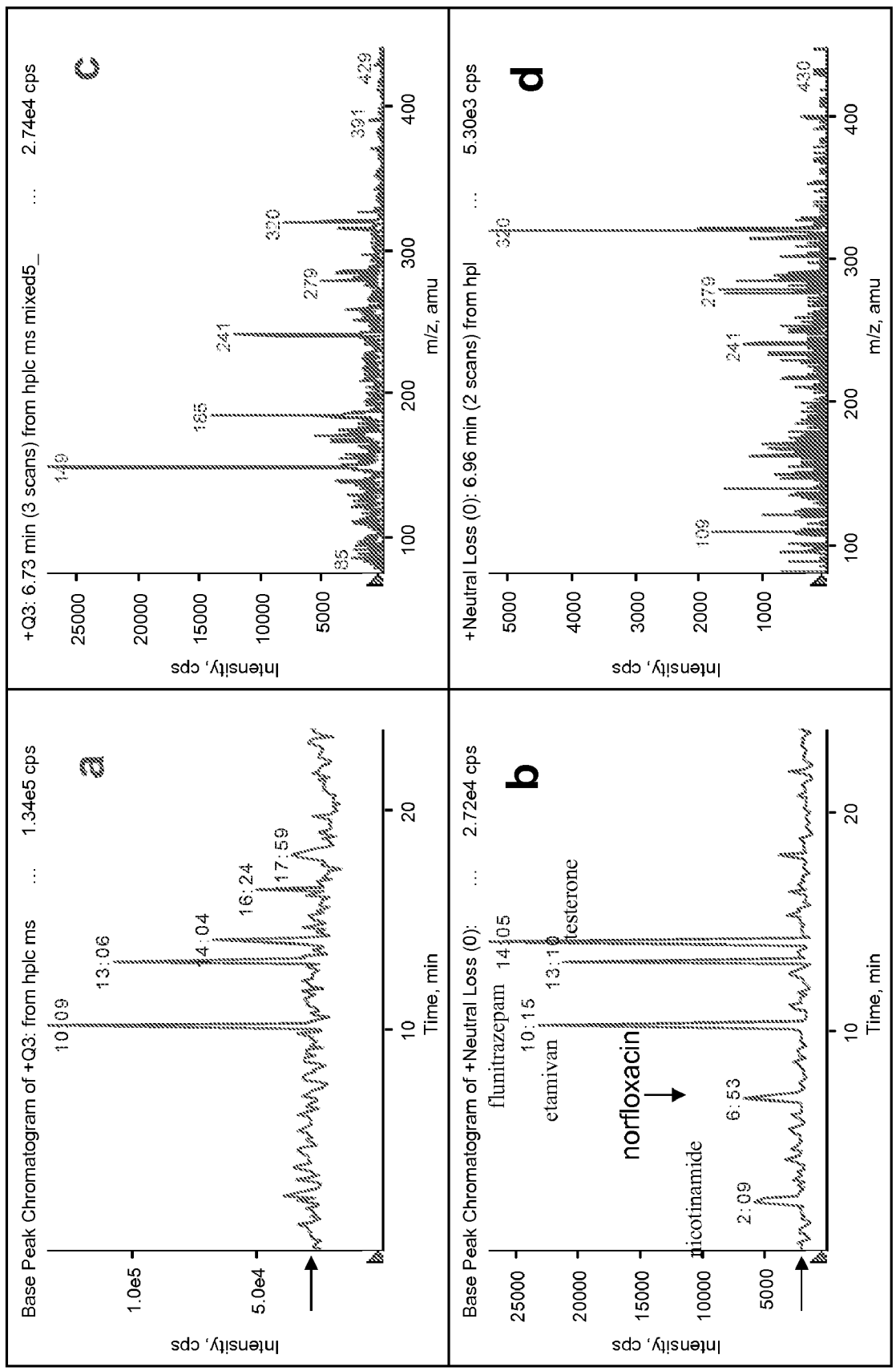
Figure 30:
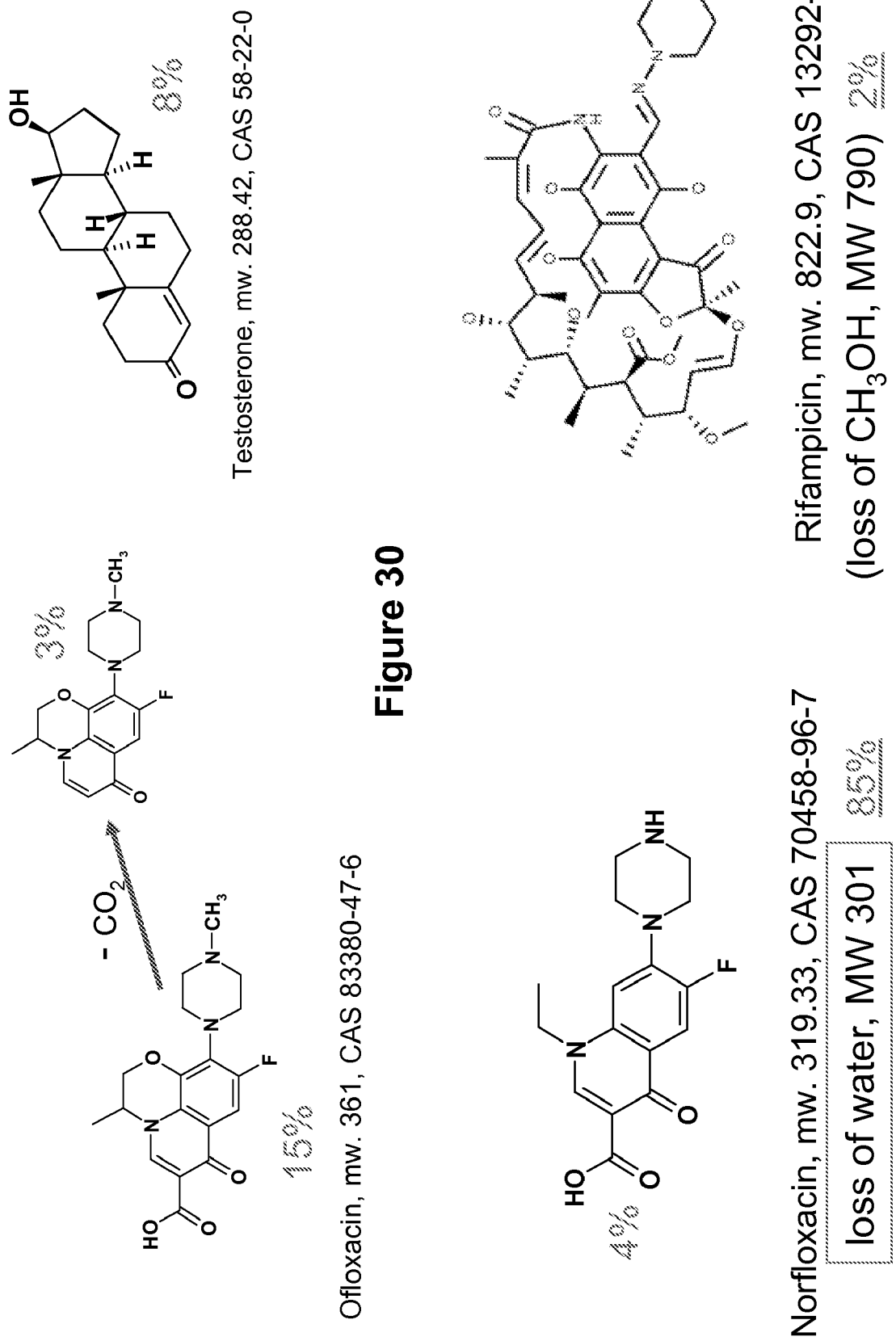
Figure 34:
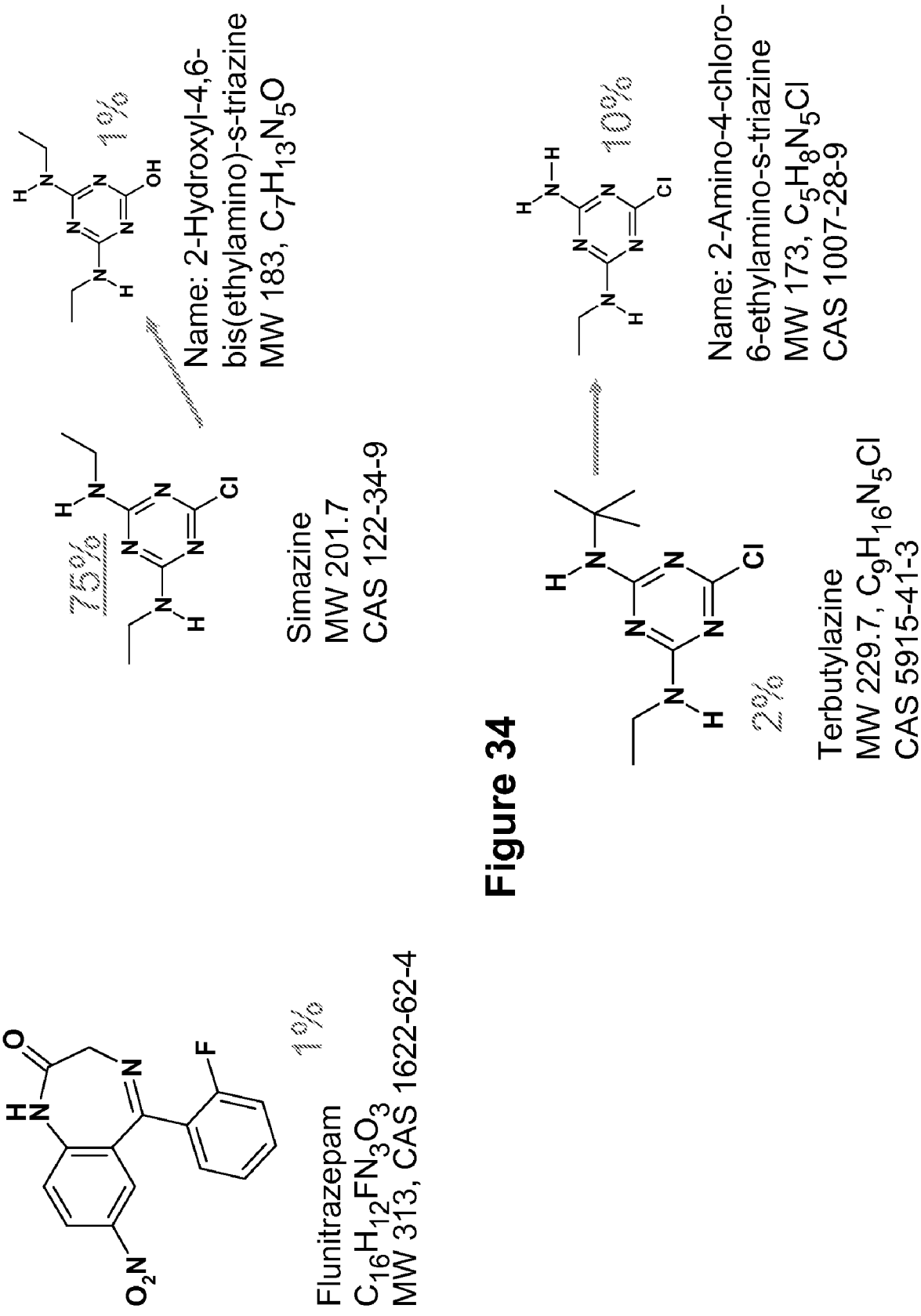
Figure 35:
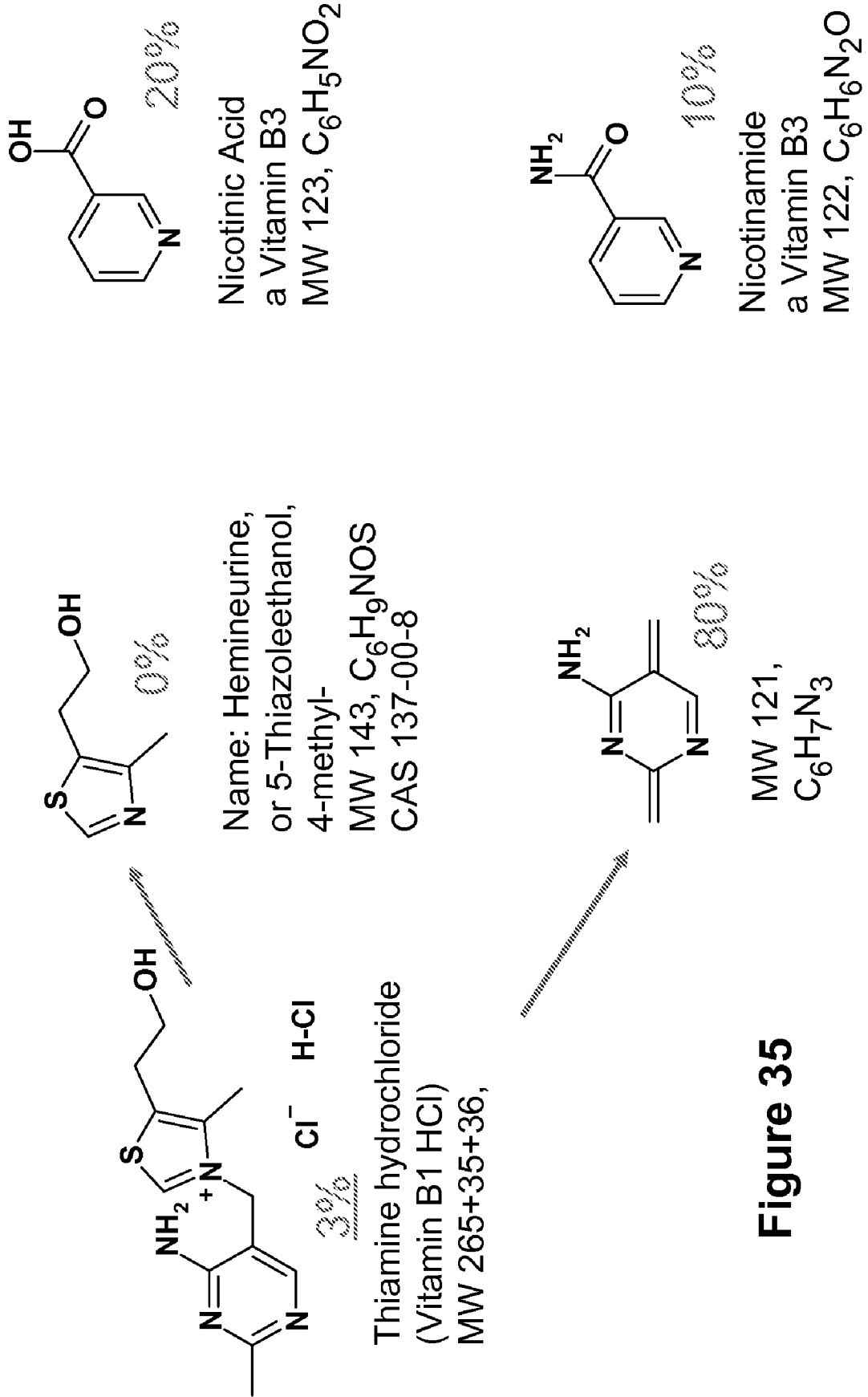
Figure 36:
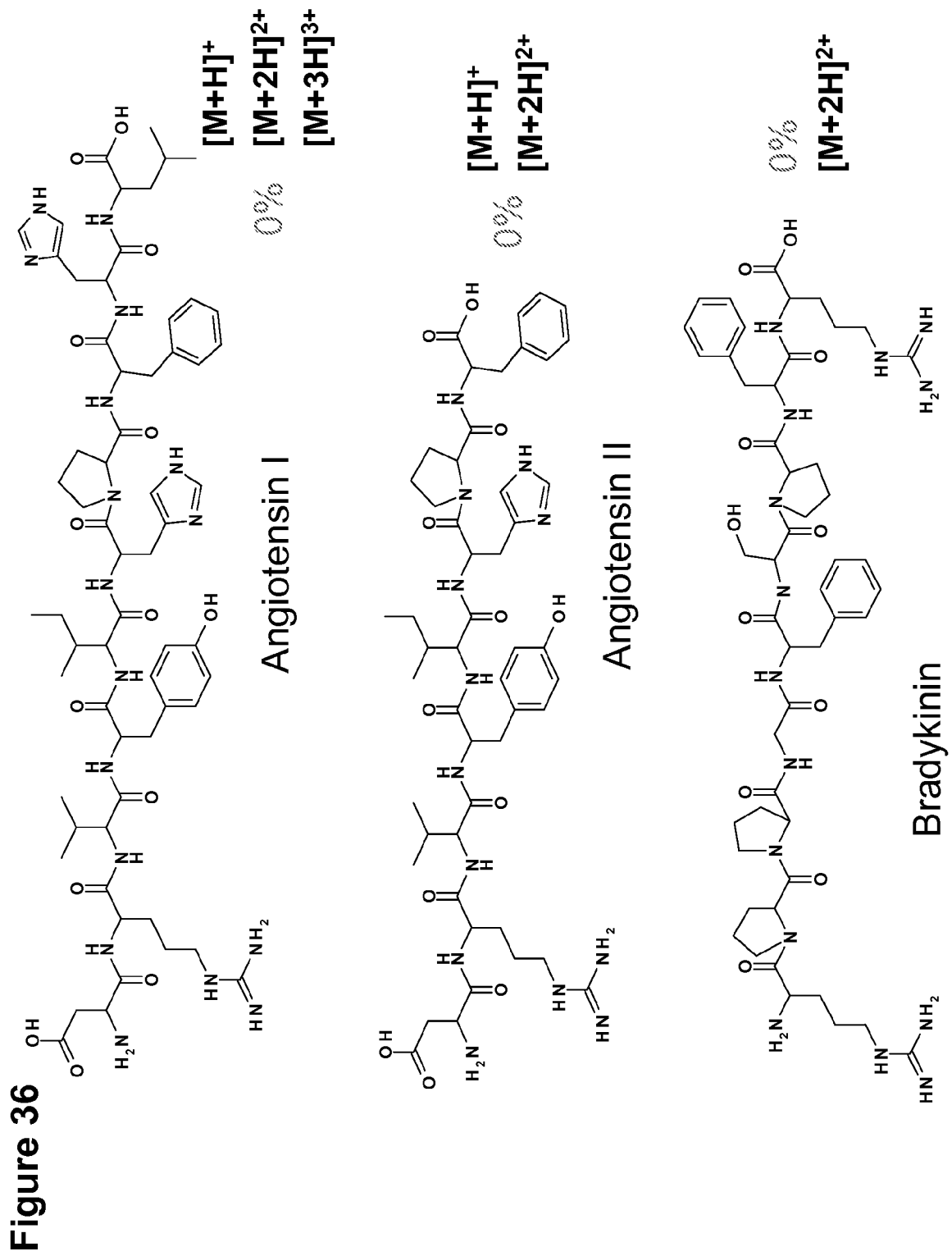
Figure 38:
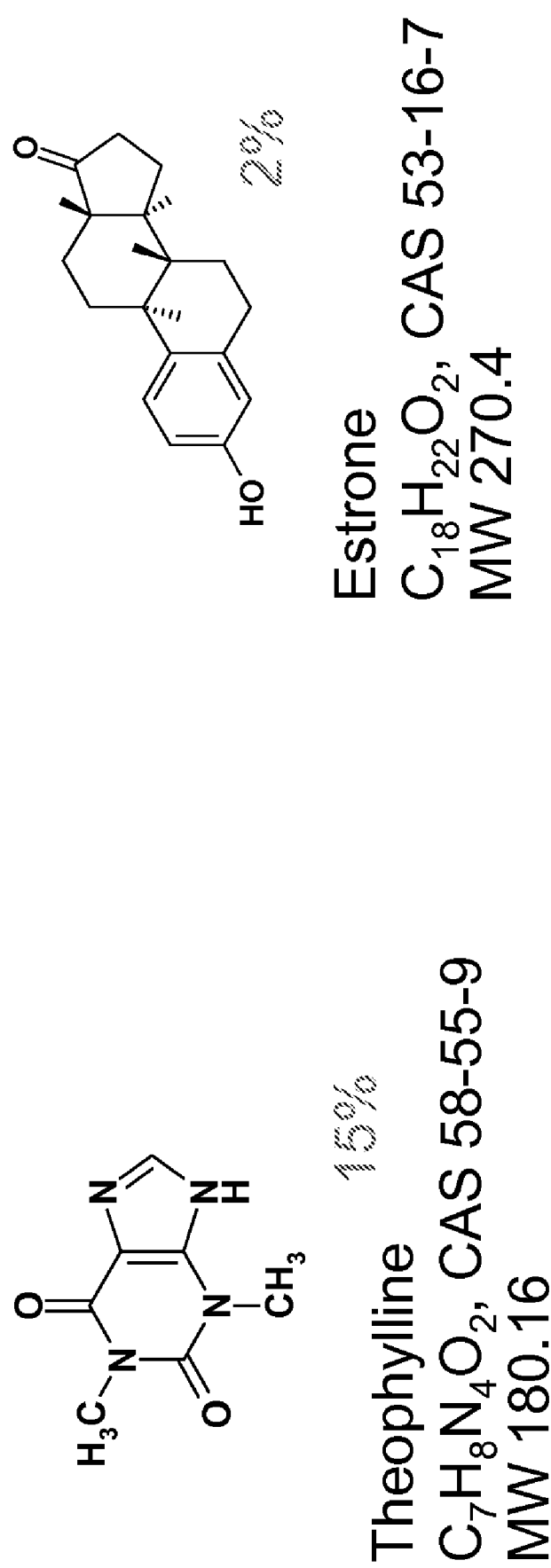

FIGS. 28A-28D depict TurboIon Spray LC/MS chromatograms and mass spectra of a mixture of eight biomolecules: nicotinamide (RT=2:12), [M+H]+=123; norfloxacin (RT=7:14), [M+H]+=320; etamivan (RT=10:20), [M+H]+=224. fludrocortisone (RT=11:24), [M+H]+=381; reserpine (RT=12:08), [M+H]+=609; flunitrazepam (RT=13:12), [M+H]+314; diazepam (RT=13:49), [M+H]+=285; and testosterone (RT=14:12), without DMDS (FIGS. 28A and 28C) and with DMDS (FIGS. 28B and 28D).

FIGS. 29A-29D depict TurboIon Spray LC/MS chromatograms (FIGS. 29A, 29B) and mass spectra (FIGS. 29C, 29D) of a mixture of five biomolecules: nicotinamide (RT=2:09), [M+H]+=123; norfloxacin (RT=6:53), [M+H]+=320; etamivan (RT=10:15)., [M+H]+=224; flunitrazepam, (RT=13:10), [M+H]+=314; and testosterone (RT=14:05), [M+H]+=289, without DMDS (FIGS. 28A and 28C) and with DMDS (FIGS. 28B and 28D).

FIGS. 30-38 depict chemical structures of various compounds listed in the tables of FIGS. 18-20.

DESCRIPTION OF VARIOUS EMBODIMENTS

In various aspects, the present teachings provide systems and methods for reducing chemical noise in a mass spectrometry instrument. In various embodiments, the methods comprise: (a) substantially excluding ions below a selected mass-to-charge ratio value (m/z) from entering a reaction region and transmitting at least a portion of the ions with a m/z value above the selected m/z value to the reaction region; (b) colliding at least a portion of the transmitted ions with a neutral chemical reagent in the reaction region; and (c) extracting from the reaction region at least a portion of ions with a m/z value in a selected m/z range and substantially excluding from extraction ions with a m/z value outside the selected m/z range; wherein the neutral chemical reagent reacts with one or more ionic species in the reaction region but does not substantially react with one or more analytes of interest transmitted to the reaction region. It is to be understood that as added into a reaction region, the neutral chemical reagent is also referred to herein as the reactive gas.

In various embodiments, the methods comprise: (a) substantially excluding ions in a selected range of ion mobility values from entering a reaction region while transmitting at least a portion of ions from the ion source with an ion mobility value outside the selected range of ion mobility values; (b) colliding at least a portion of the transmitted ions with a neutral chemical reagent in the reaction region; and (c) extracting from the reaction region at least a portion of ions with a m/z value in a selected m/z range and substantially excluding from extraction ions with a m/z value outside the selected m/z range; wherein the neutral chemical reagent reacts with one or more ionic species in the reaction region but does not substantially react with one or more analytes of interest transmitted to the reaction region. It is to be understood as used herein that term ion mobility, includes both steady-state ion mobility and differential ion mobility. The steady-state ion mobility can be represented by the equation v=KE, where v is the steady-state ion drift velocity, K is the steady-state ion mobility, also referred to as scalar ion mobility, and E is the electrical field intensity.

In the present teachings, a reaction product is preferably formed between the neutral chemical reagent and one or more background ion species, to cause the mass-to-charge ratio's of a background ion to shift to a higher or lower m/z value than the mass of the original background ion. The partial pressure of the neutral chemical reagent can be adjusted such that the ion-molecule reactions are efficient enough so that the reaction region can be coupled to the spectrometry system scan speed. In various embodiments, the present teachings combine the use of the neutral chemical reagent with the scanning and mass filtering properties of a triple quadrupole operating in the zero neutral loss (ZNL) mode, such that chemical noise ions (background ions) below the mass of the analyte, above the mass of the analyte, or above and below the mass of the analyte, are substantially ejected before reaching the reaction region (e.g., collision cell) and thus not allowed to react up into the mass channel of the analyte of interest. Chemical noise ions (background ions) isobaric with the analyte interest that react with the neutral chemical reagent gas, move to a higher or lower m/z values and can then be rejected by a mass filter (e.g. quadrupole, ion selector) situated between the reaction region and the detector of the mass spectrometry system. In various embodiments, by applying this concept with a low resolution band-pass mass or mobility filters prior to the detector, this noise reduction technique can be applied to all scan modes of a triple quadrupole by linking the scan of the filter to the scan of the first quadrupole analyzer. Collecting the chemical noise purified ion population exiting the filters in a trap can be used, for example, in various embodiments to extend the technique to all mass analyzer systems.

In various embodiments, the methods comprise: (a) substantially excluding ions in a first selected range of ion mobility values from entering a reaction region while transmitting at least a portion of ions from the ion source with an ion mobility value outside the first selected range of ion mobility values; (b) colliding at least a portion of the transmitted ions with a neutral chemical reagent in the reaction region; and (c) extracting from the reaction region at least a portion of ions with an ion mobility value in a second selected ion mobility range and substantially excluding from extraction ions with an ion mobility value outside the second selected ion mobility range; wherein the neutral chemical reagent reacts with one or more ionic species in the reaction region but does not substantially react with one or more analytes of interest transmitted to the reaction region. In various embodiments, a reaction product is formed between the neutral chemical reagent and one or more background ion species, to cause the ion mobility of a background ion to shift to a higher or lower ion mobility value than that of the original background ion.

In various embodiments the analytes of interest are organic molecules such as, for example, proteins, peptides and small molecule pharmaceuticals. In various embodiments, the analytes of interest comprise cysteine containing peptides.

In various embodiments where the background ions to be reduced or removed are positive ions, the neutral chemical reagent is preferably a nucleophile. In various embodiments where the background ions to be reduced or removed are negative ions, the neutral chemical reagent is preferably an electrophile. For example, suitable electrophiles include a molecules that have an electron withdrawing group that can attach itself to localized negative charges.

In various embodiments, the neutral chemical reagent is provided in the reaction region at an absolute pressure in the range between about $1\times10^{-4}$ torr and about 760 torr. In various embodiments, the neutral chemical reagent is provided in the reaction region at an absolute pressure in the range between: (a) about $5\times10^{-4}$ torr and about $8\times10^{-3}$ torr; (b) about $1\times10^{-3}$ torr and about $10\times10^{-3}$ torr; and/or (c) about $1\times10^{-4}$ torr and about $6\times10^{-3}$ torr.

In various embodiments, the neutral chemical reagent comprises an organic chemical species containing a disulfide functionality. Examples of disulfides include, but are not limited to, dimethyl disulfide and diethyl disulfide. In various embodiments, the neutral chemical reagent comprises an organic chemical species containing a diselenide functionality. An example of a diselenide includes, but is not limited to, dimethyl diselenide, ($CH_3Se$—$SeCH_3$); it should be noted that this compound is considered highly toxic. In various embodiments, the neutral chemical reagent comprises ethylene oxide.

In various embodiments, the neutral chemical reagent is dimethyl disulfide (DMDS) ($CH_3$—$S$—$S$—$CH_3$; DMDS; CAS no.: 624-92-0; formula: $C2H6S2$). In various embodiments of the present teachings, it has been found that when added to a collision cell, DMDS reacts with background ions that tend to be composed of clusters yet does not substantially react with many organic analytes of interest. It has been observed that the reaction of DMDS with background ions can shift the mass of the background ion (1) up by the mass of DMDS or several DMDS molecules; (2) up by the mass of a fragment of DMDS; and/or (3) down by a charge exchange process and abstraction of a portion of the background ion. As a result, once a reaction product is formed between the DMDS and a background ion species, the m/z value of the background ion will shift to higher or lower value than the mass of the original ion. Accordingly, it has been discovered that in combination with the use of the neutral chemical reagent in the reaction region, the use of a high pass mass filter before the reaction region, and a low resolution high and low mass filter (band pass filter) after reaction region can be used to remove the background ions yet leave analyte ions of interest largely undiminished. As discussed further below, the smallest mass shift observed in the examples presented herein using DMDS as a neutral chemical reagent was the production of m/z 141 from m/z 149. The etiology of this ion can be further understood by reference to FIG. 23A and accompanying text. Accordingly, in various embodiments, the width of the post-reaction mass filter is no greater than about ±8 amu.

In the present teachings, the selection of the neutral chemical reagent can be based on the chemical reactivity differences between analyte ions and chemical background ions when they react with the neutral reagent in the gas phase. It is believed, without being held to theory, that chemical background (noise) ions can be classified mainly as either cluster-related ions (e.g., due to insufficient de-clustering or re-clustering, etc.) or stable ions and their fragments of contaminants (e.g., airborne or from tubing and solvents, etc.). In LC/MC systems, for example, cluster-type ions are often HPLC solvent/buffer-related species.

In various embodiments, the reaction region comprises a collision cell. Examples of various collision cell arrangements include, but are not limited to, those illustrated in FIGS. 2A-2C. In various embodiments, the reaction region is at least partially within a mass separator or ion mobility separator of the instrument. Examples of such reaction region arrangements include, but are not limited to, those illustrated in FIGS. 3A-3C.

In various embodiments, the sample is doped with one or more of ammonium, an alkali ion (such as, e.g., sodium), or a combination thereof, to provide adduct ions of the background species. In various embodiments of a chemical reagent, it was observed that adducted background ions (.e.g., sodiated background ions, background ions adducted with ammonium, etc.) reacted with DMDS as a chemical reagent to a greater degree than adduct free background ions. In various embodiments, one or more of ammonium, alkali ion, or a combination thereof, are doped into the sample solution prior to ionization in the range between about 0.1 millimolar to about 10 millimolar.

In various aspects of the present teachings, the post-reaction region mass filter can be scanned to acquire a full spectrum or set at a particular mass range window to allow a specific analyte of interest to pass. Thus, limits of identification for qualitative analysis (e.g., full spectrum acquisition) and limits of detection for quantative determinations (e.g., SIM or MRM) can be improved by removal of background ions and thereby, e.g., increasing the signal to noise ratio.

Various embodiments of the present teachings can be used to reduce noise in mass spectrometric techniques which employ parent-daughter ion transition monitoring (PDITM), such as for example, SIM or MRM. In various embodiments, PDITM can be performed on a mass analyzer system comprising a first mass separator, and ion fragmentor (e.g., a collision cell) and a second mass separator. The transmitted parent ion m/z range of a PDITM scan (selected by the first mass separator) is selected to include a m/z value of one or more of the isobarically labeled amine-containing compounds and the transmitted daughter ion m/z range of a PDITM scan (selected by the second mass separator) is selected to include a m/z value one or more of the reporter ions corresponding to the transmitted amine-containing compound.

In various embodiments, the present teachings can provide a means of reducing the amount of unwanted ions entering an ion trap analyzer and thus, e.g., reduce space charge effects and increase the dynamic range of such a mass analyzer. Although using a scanning device in front of an ion trap can lead to a loss of duty cycle of the trap, rapid scanning and storage of the ions after the post-reaction band pass filtering of the ion population could help reduce these losses.

In various embodiments, the present teachings can be used to reduce chemical noise in mass spectrometry systems comprising a MALDI ion source. MALDI spectra, in particular in the low mass region of the spectra where small molecule molecular ions reside, are often dominated by chemical noise to a much greater extent than ESI spectra. It is believed that the majority of this chemical noise is due to matrix molecules. The problem can be so great as to preclude the use of systems using MALDI ion sources from qualitative small molecule analytical applications. In various embodiments, the present teachings can be used to reduce chemical noise post ionization, yet pre-mass analysis so a matrixless approach is not required to remove chemical noise. Examples of MALDI matrix materials for which the methods of the present teaching might be applied to reduce chemical noise arising therefrom include, but are not limited to, those listed in Table 1.

TABLE 1

| Matrix Material | Typical Uses |
|---|---|
| 2,5-dihydroxybenzoic acid (2,5-DHB) MW 154.03 Da | Peptides, neutral or basic carbohydrates, glycolipids, polar and nonpolar synthetic polymers, small molecules |
| Sinapinic Acid MW 224.07 Da | Peptides and Proteins >10,000 Da |
| a-cyano-4-hydroxy cinnamic acid (aCHCA) MW 189.04 Da | Peptides, proteins and PNAs <10,000 Da |
| 3-hydroxy-picolinic acid (3-HPA) MW 139.03 Da | Large oligonucleotides >3,500 Da |
| 2,4,6-Trihydroxy acetophenone (THAP) MW 168.04 Da | Small oligonucleotides <3,500 Acidic carbohydrates, acidic glycopeptides |
| Dithranol MW 226.06 Da | Nonpolar synthetic polymers |
| Trans-3-indoleacrylic acid (IAA) MW 123.03 Da | Nonpolar polymers |
| 2-(4-hydroxyphenylazo)-benzoic acid (HABA) MW 242.07 Da | Proteins, Polar and nonpolar synthetic polymers |
| 2-aminobenzoic (anthranilic) acid MW 137.05 Da | Oligonucleotides (negative ions) |

EXAMPLES

Aspects of the present teachings may be further understood in light of the following examples, which are not exhaustive and which should not be construed as limiting the scope of the present teachings in any way.

Figure 1:
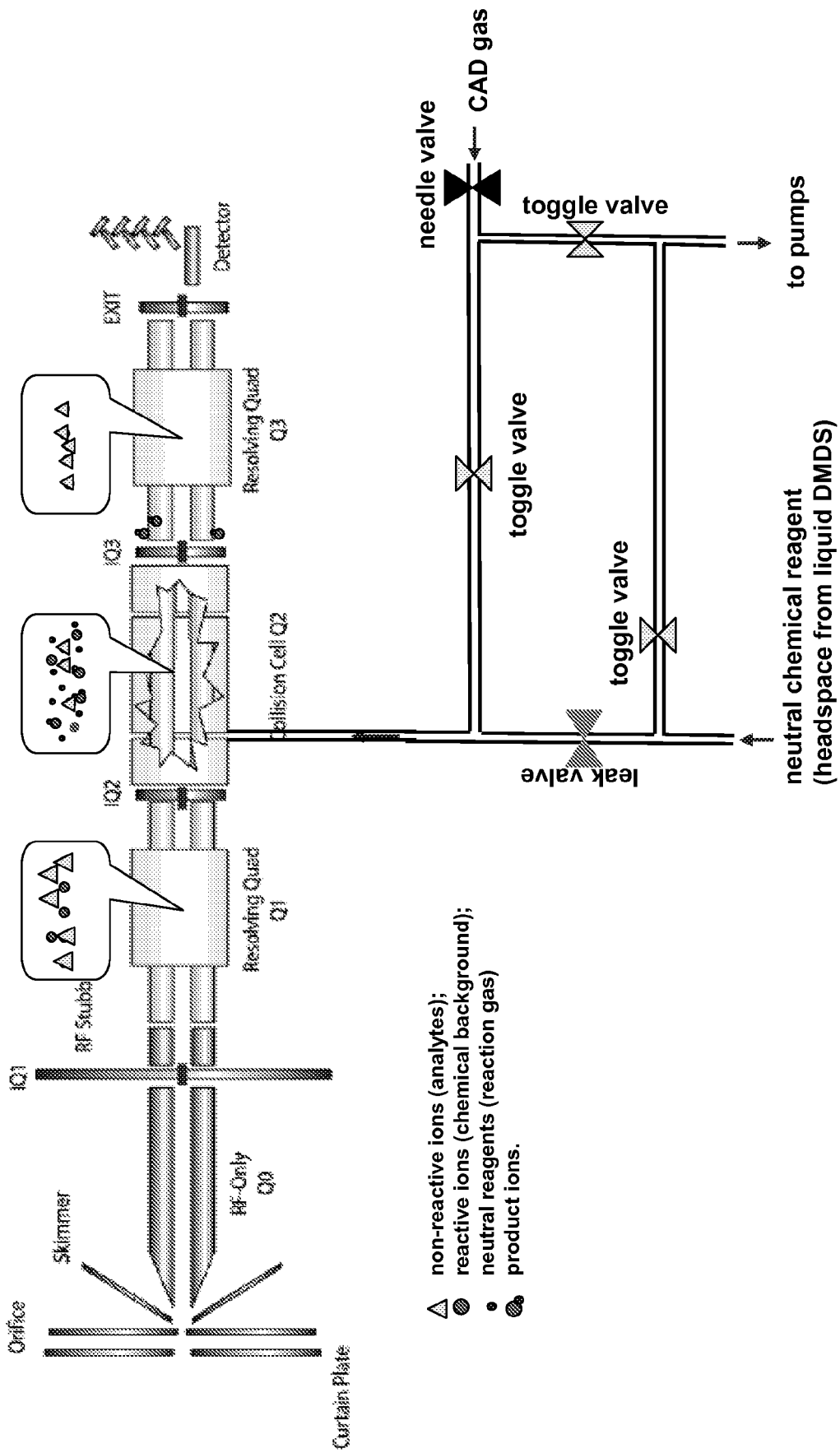

All experiments were performed on either a commercial or a custom modified triple quadrupole mass spectrometers coupled with a HPLC system (atmospheric pressure ionization, positive mode). The system used in these examples was an API 365 instrument (MDS Sciex, Inc., Concord, Ontario, Canada), which is schematically depicted in FIG. 1. The collision gas inlet was modified to allow for introduction of vapor of a liquid neutral chemical reagent (e.g., reactive collision gas) into the collision cell. To perform the noise reduction experiments, the mass spectrometer was operated in the zero neutral loss (ZNL) scan mode, which can be used to filter out ions changing m/z values after ion/molecule reactions with the neutral chemical reagent. Various LC-MS conditions and types of analytes were tested. The neutral chemical reagent used in these examples was DMDS.

The pressure readings noted in the figures and text were obtained using a Bayet Alpert gauauge mounted on the vacuum chamber of the mass spectrometer, the chamber containing Q1, Q2 and Q3 in FIG. 1. Under normal Q1 scan operating conditions (no chemical reagent added) the readout on the gauge was about $6 \times 10^{-6}$ torr. When DMDS was introduced the pressure at the gauge increased to about $1.3 \times 10^{-5}$ torr. It should be noted that these pressure readings have not been corrected for the difference in response of the gauge to DMDS and nitrogen. Accordingly, the pressure increment (of about $0.7 \times 10^{-5}$ torr in this example) is what is referred to as the "partial pressure" of DMDS. The pressure inside the collision cell was estimated to be a few millitorr for these operating conditions and instrument. In principle, without being held to theory, only a single collision between a neutral chemical reagent molecule and background ion can be sufficient for reaction to occur.

Unless otherwise noted, a "partial pressure" of about $0.7 \times 10^{-5}$ torr of DMDS (as described above) was used in the data of this example where DMDS was added.

FIGS. 4A-17 present examples of the data obtained. A further understanding of the data in these figures can be had from consultation of the text and notations made thereon and the brief descriptions previously presented. FIGS. 18-20 provide a summary in tabular form of the reactivity of the chemical regent with various analytes and compounds.

Figure 4A:
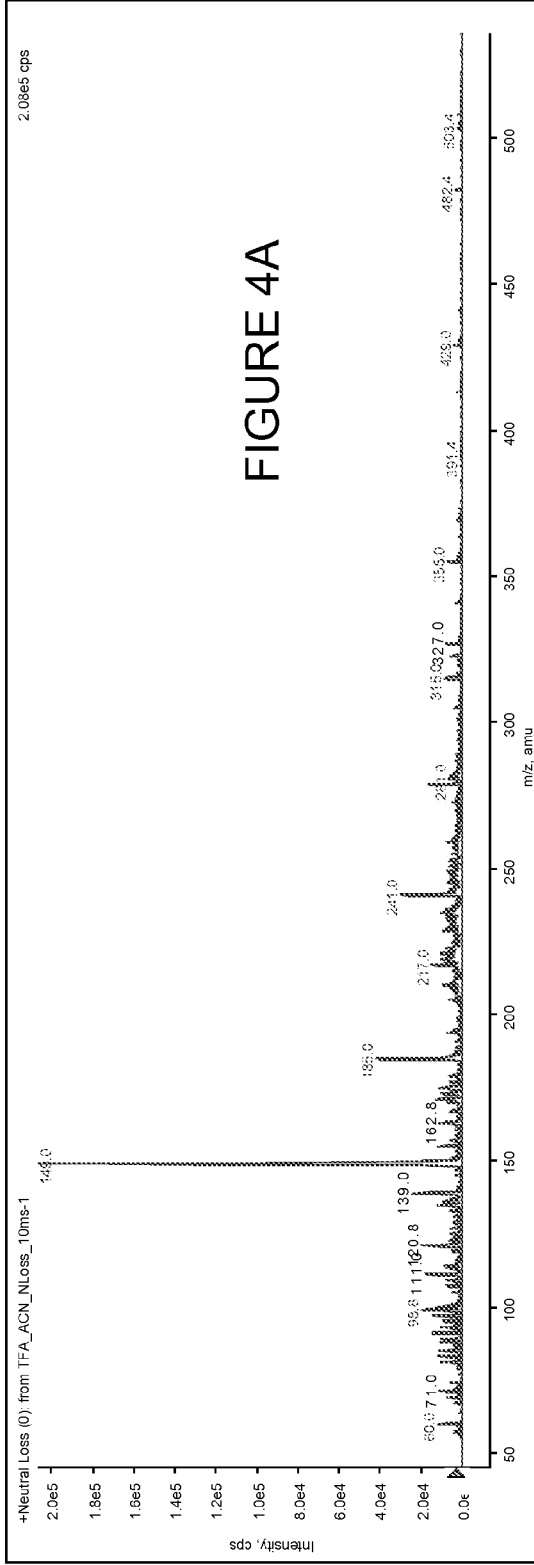
Figure 4B:
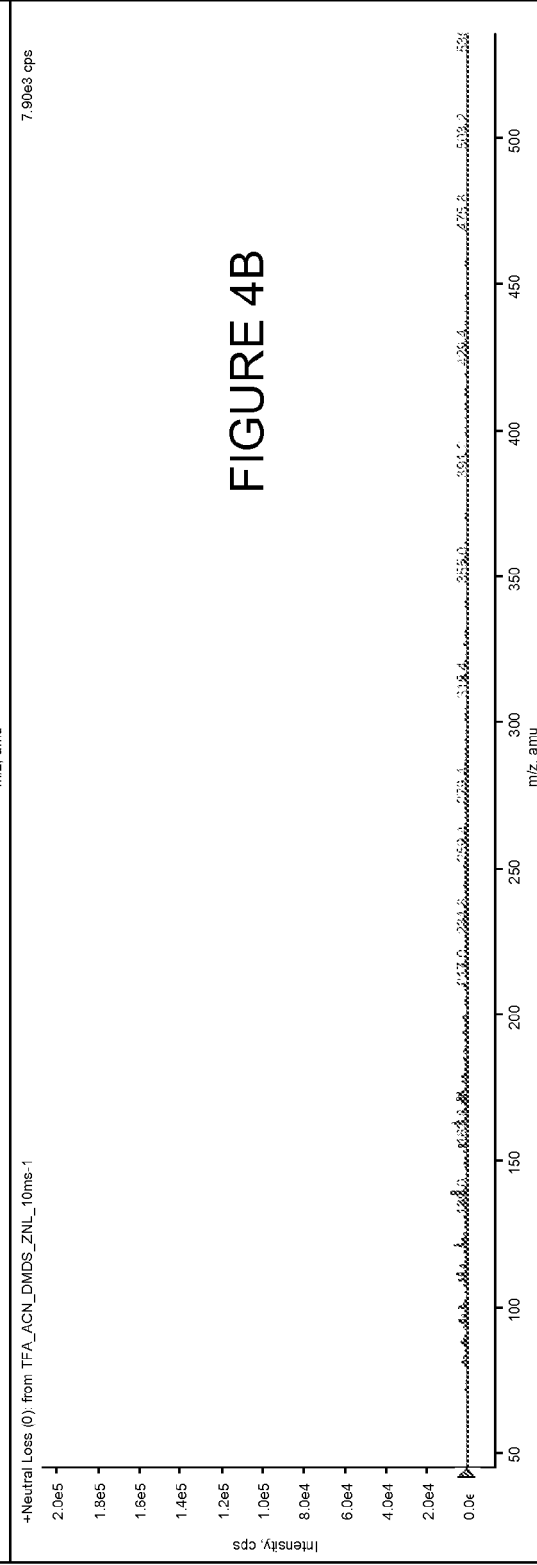

FIGS. 4A-4B present electrospray mass spectra of the chemical background spraying of ACN/H$_2$O/TFA in the approximate ratio of 50:50:0.1. FIG. 4A depicting mass spectra without DMDS reaction gas and FIG. 4B mass spectra with the addition of DMDS to the collision cell. The reactions occur with an estimated 95% of the total chemical background ions from this LC/MS mobile phase and others tested with electrospray ionization. The results indicate that a partial pressure readout on the Bayart Alpert gauge mounted on the vacuum chamber of the mass spectrometer of about $0.7 \times 10^{-5}$ torr of DMDS, which corresponds to about $3 \times 10^{-3}$ torr in the collision cell of this instrument, can induce at least one step of reactions between the chemical background ions and the DMDS.

FIG. 5 depicts the effect on the total ion current (TIC) when DMDS was applied and ZNL scanning. FIGS. 6A and 6B depict, respectively, mass spectra under the conditions of regions (a) and (c) of FIG. 5. The ions were generated with an electrospray of ACN:iso-propanol:HCOOH. The regions in FIG. 5 correspond to the following: (a) DMDS added to cell at a "partial pressure" (as described above) of about $0.7 \times 10^{-5}$ torr; (b) no gas added to cell with a background pressure at the gauge of $0.6 \times 10^{-5}$ torr; and (c) only nitrogen added to the cell, with a pressure on the gauge of $0.7 \times 10^{-5}$ torr.

About a 10× reduction in the TIC is observed in this case attributed to the DMDS and not to additional declustering afforded by the nitrogen. The TIC remained almost the same between conditions (b) and (c) in FIG. 5 which indicates the reduction in (a) of chemical background is due to DMDS. Similar effects have been observed for a variety of other commonly used LC mobile phases.

The data of FIGS. 7A-17 were acquired in the zero neutral loss (ZNL) mode. Data noted as without DMDS, were acquired with nitrogen in the collision cell, and data noted as with DMDS were acquired with DMDS in the collision cell. Data presented, showing the reaction products and/or the extent of reaction of DMDS with the various compounds tested, were obtained by acquiring a product ion spectrum of the molecular ion of interest with DMDS in the cell, at very low collision energy (e.g., 2 eV), and scanning above and below the mass of the parent ion.

Prazepam

FIGS. 7A-7B and 8, present data on prazepam (C19H17ClN2O; MW 324.1) a high proton affinity compound whose structure is schematically illustrated as an inset in FIGS. 7A and 8. FIG. 7A presents a Prazepam ZNL MS spectra without DMDS and FIG. 7B with DMDS added as a neutral chemical reagent for chemical noise reduction. FIG. 8 mass spectral data used to ascertain the extent of reaction of DMDS with prazepam ([M+H]$^+$); using a product ion scan of m/z 325 scanning Q3 from about 200 m/z to about 500 m/z with DMDS in collision cell. The reactivity of DMDs with prazepam was observed to be less than about 1%.

Midazolam

FIGS. 9A-9C present data on midazolam (C18H13ClFN3; MW 325) a high proton affinity compound whose structure is schematically illustrated as an inset in FIG. 9A. FIG. 9A presents a midazolam ZNL MS spectra without DMDS and FIG. 9B with DMDS added as a neutral chemical reagent for chemical noise reduction. FIG. 9C (inset in 9B plot) shows mass spectral data used to ascertain the extent of reaction of DMDS with midazolam ([M+H]$^-$); using a product ion scan of m/z 325 scanning Q3 from about 200 m/z to about 500 m/z with DMDS in collision cell. No reaction products were observed.

Fludrocortisone

FIGS. 10A-11B present data on fludrocortisone (MW 380.2), a low proton affinity compound, whose structure is schematically illustrated as an inset in FIGS. 10A and 11B.

FIGS. 10A-10B compare ZNL mass spectra of fludrocortisone without DMDS (FIG. 10A) and with (FIG. 10B) and added to the collision cell. Background is reduced and the molecular ion remains substantially unattenuated. The sodium adduct [M+Na]$^+$, at m/z=403, is observed to be reduced relative to the protonated fludrocortisone [M+H]$^+$.

FIGS. 11A-11B assess reactions of fludrocortisone with DMDS using the product ion scan method, Figure. Two thirds of the [M+Na]$^+$ ion (m/z about 403) were observed to react with the reagent DMDS (producing peak at about m/z 497, circled by a dashed line in FIG. 11A) (see data of FIG. 11A). The protonated fludrocortisone ion [M+H]$^+$ (m/z about 381) showed less than 5% reactivity (reaction product about m/z 475 circled by a dashed line in FIG. 11B)(see data of FIG. 11B).

Estrone

FIGS. 12A-12B compare ZNL mass spectra of estrone (C18H22O2, MW 270.4), a relatively low proton affinity compound, whose structure is schematically illustrated as an inset in FIG. 12B. FIG. 12A presents data without DMDS and FIG. 12B with DMDS added to the collision cell. The ammonium adduct of estrone [M+NH$_4$]$^-$ (m/z about 288) shows approximately a 30% attenuation, while the sodium adduct [M+Na]$^+$ (m/z about 293) was reduced significantly. The background reduction was also extensive. It was also observed that protonated estrone [M+H]$^+$ (m/z about 271) and the ammonium adduct do not loose substantial ion current but that the sodium adduct does loose substantial ion current upon addition of DMDS.

Flunitrazepam

FIGS. 13A-13B assess reactions of protonated and sodiated flunitrazepam (C16H12FN3O3, MW 313) with DMDS using product ion scanning. The chemical structure of flunitrazepam is schematically depicted by the inset in FIG. 13A.

Protonated flunitrazepam [M+H]$^+$ (m/z about 314) was observed to substantially not react to form products with DMDS (m/z about 408) (see data of FIG. 13A). The sodium adduct, [M+Na]$^+$ (m/z about 336) was observed to react to a similar extent (reaction product at about m/z 430 and circled by a dashed line in FIG. 13B) as observed for fludrocortisone (see data of FIG. 13B).

Etamivan

FIGS. 14A-14B assess reactions of protonated and sodiated etamivan (MW 223.3) with DMDS using product ion scanning. The chemical structure of etamivan is schematically depicted by the inset in FIG. 14A.

Protonated etamivan [M+H]$^+$ (m/z about 224) was observed to substantially not react to form products with DMDS (see data of FIG. 14A). The sodium adduct, [M+Na]$^+$ (m/z about 246) was observed to react to a similar extent (reaction product at about m/z 340 and circled by a dashed line in FIG. 14B) as observed for fludrocortisone and flunitrazepam (see data of FIG. 14B).

Cyclosporine A

FIGS. 15A-15B compare ZNL mass spectra of cyclosporine A (MW 1202.6), a relatively low proton affinity peptide (no basic residues) without DMDS (FIG. 15A) and with DMDS (FIG. 15B) and added to the collision cell. The chemical structure of is cyclosporine A schematically depicted by the inset in FIG. 15B. The double protonated cyclosporine ion [M+2H]$^{2+}$, at about m/z=602, appears to have gained signal in the presence of DMDS. The satellite ions (1502) to the doubly charged ion are the Na and K adducts. The Na adduct is reduced relative to the other molecular ions to a greater extent by the DMDS but the effect does not to be as great as with the previous small molecule examples.

Angiotensin II

FIGS. 16A-16D and 17 present data for angiotensin II. The chemical structure of angiotensin II is schematically depicted by the inset in FIG. 17.

FIGS. 16A-16D compare angiotensin II background reduction with DMDS under various conditions, where the angiotensin II was ionized by ESI from a mobile phase of methanol:water:acetic acid in the approximate ratio of 50:50:0.1.

FIGS. 16A (a) and 16B (b) compare a Q3 single MS scan (with N2 in the collision cell) with a zero neutral loss with nitrogen. This comparison shows that the ion current is reduced by about 2.5-3× by virtue of transmission losses to be expected when operating two RF/DC quadrupoles instead of one. Mainly background ions were observed fr the conditions of FIG. 16A. FIG. 16C (c) shows the effect of DMDS at a partial pressure (as described above) of about $0.7 \times 10^{-5}$ torr. No signal attenuation of the double protonated analyte [M+2H]$^+$ is observed (compare to 16B (b)) while background reduction is observed to occur. Fragment ions (e.g., $y_2$+, $a_5$+, $a_6$+, $b_5$+and $b_6$+)were seen in both cases (b) & (c). A measurement at a higher DMDS partial pressure (as described above) of about $1.0 \times 10^{-5}$ torr was not observed to improve the spectra and attenuate the signal by about a factor of 4.

FIG. 17 depicts a product ion scan of the [M+2H]$^{2+}$ ion of angiotensin II with DMDS in the collision cell and a 2 eV collision energy. No reaction of angiotensin II with DMDS was observed.

Further Data

FIGS. 18-20, present, respectively, tables with data on other molecules tested. Chemical structures of various compounds listed in the tables of FIGS. 18-20 are presented in FIGS. 30-38. Tables 18-20 summarize the reactivity to DMDS of 41 compounds with widely varying chemical properties and functional groups. Ten of these compounds produced fragments as well as protonated molecular ions and the reactivity of the fragments is included. The reactivity of the sodium adducts as well as other unidentified adducts is also presented. Of the 41 species the majority (30) reacted less than 5%. Thirty eight of the 41 reacted less than 20%. Three of the 41 tested compounds "reacted" substantially (between 20-25% reacted). Only one of these three compounds reacted by adduction. The other two compounds did not react, but fragmented via CID channels. The majority of the compounds that produced sodiated species showed a high reactivity (>65%) toward that adduct.

In Tables 1-3 (FIGS. 18-20), the second column gives the name of the compound tested; the third column provides a list of likely reaction site for reaction with DMDS. The fourth column indicates the approximate m/z value of the protonated compound and in parenthesis the approximate percentage of the protonated compound that reacted with DMDS; the fifth column indicates the approximate m/z value of the sodiated compound (sodium adduct) and in parenthesis the approximate percentage of the sodiated compound that reacted with DMDS; the sixth and last column list the reaction of various other ions where the number is the ion's approximate m/z value and the number in parenthesis is the approximate percentage of that ion that reacted with DMDS.

The underlined numbers represent those losses arising from dissociation of the ion and not necessarily adduct formation with DMDS. The superscript to a mass indicates the charge stat of the ion, e.g., cyclosporine A was observed in a double charge state (602, where m=1204 and z=2+) and a singly charged state (m/z=1203).

In the experiments it was observed that major chemical background ions reacted with the neutral chemical reagent, Dimethyl Disulfide (DMDS, CH3S—SCH3), to form adduct ions and fragments thereof. The majority of the tested protonated analytes, such as the tested peptides including cysteine containing peptides and multiply charged protonated species, small molecule pharmaceuticals and other biomolecules, did not react significantly with DMDS to the same extent that DMDS reacted with the background ions. It was observed that sodiated molecular ions, [M+Na]$^+$, reacted to a greater degree than protonated [M+H]$^+$ or [M+NH$_4$]$^+$ions on all compounds tested in these experiments.

Background Ions

FIGS. 21A-24B present data obtained on the reaction of the neutral chemical reagent of these examples, DMDS, with various background ions. The data were obtained using product ion scans of targeted background ion species, adding reactive gas to the cell, and scanning above and below the mass of the parent background ion. The data show that the vast majority of electrospray background ions from typical LC solvents react with DMDS.

FIGS. 21A-21C assess the reactions of the background ion m/z 99 at different partial pressures (as describe above) of DMDS using product ion scanning above and below the mass of the targeted ion. This m/z=99 ion was determined to be P(OH)$_4^+$ and is schematically illustrated, e.g., in FIG. 26. The data are for the electrospray ionization of the output from an LC column with a mobile phase of methanol:water:acetic acid in the approximate ratio of in the approximate ratio of 50:50:0.1.

FIG. 21A shows data for a DMDS partial pressures of about $0.4 \times 10^{-5}$ torr; FIG. 21B of about $0.7 \times 10^{-5}$ torr; and FIG. 21C of about $1.0 \times 10^{-5}$ torr as measured at the Bayet Alpert gauge as described above. The m/z values for water clusters [M+nH$_2$O]$^+$, single DMDS adduct water clusters [M+DMDS+nH$_2$O]$^+$, double DMDS adduct waters clusters [M+2*DMDS+nH$_2$O]$^+$, triple DMDS adduct waters clusters [M+3*DMDS+nH$_2$O]$^+$, and DMDS a clusters [M+n*DMDS]$^+$,are indicated in the figure for ease of evaluation.

FIGS. 22A-22D assess the reactions of four background ions as indicated in the figure header, m/z=83, m/z=115, m/z=143, and m/z=159, respectively. The data are for the electrospray ionization of the output from an LC column with a mobile phase of methanol:water:acetic acid in the approximate ratio of in the approximate ratio of 50:50:0.1; and a partial pressure of about $0.7 \times 10^{-5}$ torr of DMS was used as described above.

The reactions were observed to be dominated by the formation of DMDS adducts [M+n*DMDS]$^+$ with up to three neutral DMDS molecules, combined with addition of water molecules, e.g., [M+nH$_2$O]$^+$. Water can arise as an impurity in the DMDS and/or as present in the vacuum background. Various reactions of these ions are illustrated in FIGS. 25 and 26.

FIGS. 23A-F assess the reactions of an additional six background ions which did not show extensive adduction but proceed by charge transfer. The spectra of FIGS. 23A-F are, respectively, the product ion scans of (a) m/z 149; (b) m/z 60; (c) m/z 78; (d) m/z 83; (e) m/z 99; and (f) m/z 205. The data are for the electrospray ionization of the output from an LC column with a mobile phase of methanol:water:acetic acid in the approximate ratio of in the approximate ratio of 50:50:0.1; and a partial pressure of about $0.7 \times 10^{-5}$ torr of DMS was used as described above.

A charge exchange reaction of the DMDS adduct with the background ion is observed to occur resulting in m/z 141= [DMDS +$SCH_3$]$^+$. It is believed to arise by the adduction of several DMDS molecules to the ion followed by charge exchange to and fragmentation of the DMDS dimer. This can be an important mechanism to remove phatlates (m/z=83, 149 and 205 in this example). For example, m/z=149 corresponds to a phthalate background ion that is ubiquitous in most electrospray spectra. The conversion of 149 to 141 in the spectrum can be used, for example, to set a minimum band width of a post-reaction bandpass mass filter. In the examples, the bandpass width was 1 amu for both pre and post reaction region filters when the mass spectrometer system was used in zero neutral loss (ZNL) mode.

FIGS. 24A-B schematically depicts a summary of the reactivity and believed reaction channels of the background ions in a typical ESI spectrum of this example from a LC column with a mobile phase of methanol:water:acetic acid in the approximate ratio of in the approximate ratio of 50:50:0.1; and a partial pressure of about $0.7 \times 10^{-5}$ torr of DMS as described above.

A few of the background ions showed substantially no reactivity (circled ions). A legend describing the various reactions leading to various observed peaks is inset below the spectra, where the solid line indicates addition of neutral DMDS, the dotted line addition of water, the diamond-headed line the addition of $SCH_3$ or $HSCH_3$ and the circle indicating ions that showed substantially no reactivity with DMDS. FIG. 24B obtained by neutral gain scan (DMDS present in the cell) shows the chemical background ions that react with at least one DMDS to gain a mass of 94.

The identity of many of the background ions has also been elucidated by MS/MS. FIGS. 25 and 26 schematically summarize a study undertaken to identify common background ions using various MS/MS scan modes and to establish the relationships among the background ion populations. The results are presented as possible "family trees" of chemical background ions commonly observed from API-LC/MS mobile phases ACN/H2O/HCOOH and MeOH/H2O/CH3COOH.

The numbers in FIGS. 25 and 26 refer to the m/z value of a singly charged ion. The results obtained in these experiments indicate that the majority of the major chemical background ions are either stable ions (or fragments thereof) of contaminants, such as adipates, sebacates, phthalates, phenyl phosphates, silicones and their derivatives (e.g., airborne, from the tubing and/or mobile phases, etc) as shown, e.g., in FIG. 25; or cluster related ions (e.g., solvent/buffer involved) as shown, e.g., in FIG. 26. The cluster related ions mostly have some ions from contaminants as nuclei. The neutral molecules of water, methanol, acetonitrile, and acetic acid are found to be involved in clustering. Although the intensity and/or appearance of some background ions can vary under different LC/MS experimental conditions, most observed cluster-related background ions in these experiments were relatively stable and survived the declustering conditions in the ion source and entrance optics.

Mixtures of Analytes

FIGS. 27A-29D present chromatographic data and data on mixtures of analytes of interest. The data were obtained using a TurboIon Spray source off the LC/MS.

FIGS. 27A-27F depict TurboIon Spray LC/MS mass spectra of four pharmaceutical compounds, at 200 μL/min, nicotinamide, etamivan, flunitrazepam, and testosterone, without DMDS (FIGS. 27A, 27B and 27C) and with DMDS (FIGS. 27D, 27E and 27F). In FIGS. 27A-27F, neutral loss scanning was performed for the background reduction acquisition and Q3 single MS scans were performed for the standard acquisition. Under these operating conditions, approximately a factor of 2-3 loss in signal is expected due to transmission differences so, for comparison purposes, the TIC baseline is overestimated for the non-background reduced chromatogram as is the analyte signal in the spectra.

FIG. 27A shows a base-peak chromatogram (Q3 scan) before addition of DMDS, and FIG. 27D after. It can bee seen that in the ZNL scan after the introduction of DMDS (FIG. 27D) the substantial reduction in background and baseline noise (compare for example portions circled by a dashed line) and the observation of nicotinamide and testosterone.

FIGS. 27B and 27E compare the noise reduction in chemical background mass spectra of the TIC region between about 3 to about 8 min, a region anticipated to contain some common contaminants, e.g., phthalates such as m/z=149. The reduction in chemical background noise is clear.

FIGS. 27C and 27F compare the noise reduction of the TIC region at about 17.38 min (the approximate retention time of testosterone in this experiment). The in crease in signal-to-noise testosterone (m/z about 289) after introduction of DMDS is clear as well as a change in the mass spectra. The signal level in the background reduced testosterone spectrum FIG. 27F (7000 cps) was observed to be approximately 3× lower than in the non-background reduced spectrum FIG. 27C (25,000 cps). What is not accounted for by transmission loss (2-3×) and reactivity of testosterone with DMDS (a reactivity of about 8% was expected, see e.g., FIG. 18) is believed to be due to the removal of isobaric interferences from the background ions.

FIGS. 27A-27F provide an example of a practical application of the neutral chemical reagent DMDS for the reduction of chemical background noise in LC-MS. FIGS. 27A-27F can be used as an example of the ability of various embodiments of the present teaching to be used in providing base peak chromatograms. Base peak chromatograms are often used to reveal the trace components in LC-MS analysis to localize/identify unknown species. This approach can be used, e.g., to reduce or prevent the significant contribution of chemical background ions to a TIC, which can, e.g., totally overshadow the appearance of those low abundant analytes. In an automatic identification or screening process with LC-MS it can be important to trigger a tandem MS/MS scan to acquire further information on structures. Such scans are often triggered to perform MS/MS experiments on the base peak or the most intense ones. However, if the intensities of the trace components are already lower than that of the major (base peak) chemical background ions in a mass spectrum, these minor analytes will not be identified and picked up for a further MS/MS experiment.

FIGS. 27A-27F show that, after the chemical noise reduction with DMDS according to the present teachings, the two minor components nicotinamide (at about the retention time 2.23 min., i.e., 2 minutes, 14 seconds) and testosterone (17.47 min., i.e., 17 minutes, 28 seconds) are detected, see, e.g., FIG. 27D, in contrast to the analysis without the chemical noise reduction, see e.g., FIG. 27A. The signal-to-noise ratio of the peaks in the base peak chromatogram improves by about a factor of 10-20. The fluctuating baseline before the noise reduction (circled portion on the right hand side of FIG. 27A) becomes a relatively flat line after the noise reduction (circle portion on the right hand side of FIG. 27D). The change of the mass spectra of the component testosterone before and after the DMDS noise reduction (FIGS. 27C and 27F respectively) illustrates that background ions have been removed from the TIC.

FIGS. 28A-28D depict TurboIon Spray LC/MS mass spectra of a mixture of eight biomolecules: nicotinamide (RT=2: 12), [M+H]+=123 (2801); norfloxacin (RT=7:14), [M+H]+=320 (2802); etamivan (RT=10:20)., [M+H]+=224 (2803); fludrocortisone (RT=11:24), [M+H]+=381 (2804); reserpine (RT=12:08), [M+H]+=609 (2805); flunitrazepam (RT=13: 12), [M+H]+314 (2806); diazepam (RT=13:49), [M+H]+=285 (2807); and testosterone (RT=14:12) (2808), without DMDS (FIGS. 28A and 28C) and with DMDS (FIGS. 28B and 28D).

The data before addition of DMDS is a Q1 full scan acquisition and the data after DMDS addition is a zero neutral loss (ZNL) scan. A 2-3× reduction in transmission efficiency is expected and partially accounts for the difference in counts on the molecular ions; removal of isobaric interferences is a possibility as well.

FIGS. 28A and 28B show that before noise reduction using the present teachings, only two of the eight biomolecules are detected (FIG. 28A), but that after (FIG. 28B) all eight are observed. FIGS. 28C and 28D compare the spectra observed for the TIC region around 10:20, elution of etamivan. The addition of DMDS according to the present teachings, can be seen to have increased the protonated etamivan signal (m/z about 224) and decreased the relative proportion of fragmentation (e.g., peak at about m/z 149 in FIG. 28C and peak at about m/z 151 in FIG. 28D).

FIGS. 29A-29D depict TurboIon Spray LC/MS chromatograms (FIGS. 29A, 29B) and mass spectra (FIGS. 29C, 29D) of a mixture of five biomolecules: nicotinamide (RT=2:09), [M+H]+=123; norfloxacin (RT=6:53), [M+H]+=320; etamivan (RT=10:15), [M+H]+=224; flunitrazepam, (RT=13:10), [M+H]+=314; and testosterone (RT=14:05), [M+H]+=289, without DMDS (FIGS. 29A and 29C) and with DMDS (FIGS. 29B and 29D). The mixture comprised about 10 ng of each biomolecule. The data before addition of DMDS is a Q3 single MS scan with nitrogen gas and the data after DMDS addition is a zero neutral loss (ZNL) scan. It is to be understood that in FIGS. 29C and 29D, the loss of norfloxacin signal (9000->5000cps) largely due to transmission losses due to the change in scan mode.

FIGS. 29A and 29B compare TIC chromatograms and demonstrate the ability, in various embodiments, of the present teachings to reveal signals otherwise obscured by noise. For example, by the neutral chemical reagents of the present inventions reacting with one or more contaminants but not substantially reacting with one or more analytes of interest. For example, two trace components (nicotinamide and norfloxacin) at the retention times of 2.15 and 6.90 min., respectively, where detected in the basepeak chromatogram after the chemical noise reduction with DMDS (see FIG. 29B) that were note observed before (se FIG. 29A).

FIGS. 29C (without DMDS) and 29D (with DMDS) compare the spectra observed for the TIC region around 6.96 min., elution of norfloxacin. The addition of DMDS according to the present teachings, can be seen to have increased the protonated norfloxacin signal (m/z about 320) and relative to the noise.

FIGS. 30-38 depict chemical structures of various compounds listed in the tables of FIGS. 18-20. In addition, FIGS. 30-38 summarize some of the data regarding the reaction of the protonated forms of these compounds with DMDS. The percentage listed next to structure indicate the observed reactive percentage of the protonated molecule. Underlined percentages indicate the reactions are dissociations. In some instances, analogs derived from a compound in the list were also studied and their reaction percentage are also indicated, e.g., such as loss of water from a hydrated analog.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While the teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto, are claimed. The descriptions and diagrams of the methods, systems, and assays of the present teachings should not be read as limited to the described order of elements unless stated to that effect.

What is claimed is:

1. A method for reducing chemical noise in a mass spectrometry instrument, comprising the steps of:
substantially excluding ions in an ion source below a selected mass-to-charge ratio value (m/z) from entering a reaction region while transmitting at least a portion of ions from the ion source with a m/z value above a selected m/z value to the reaction region, the ions in the source comprising one or more background ions and one or more analytes of interest;
changing the m/z value of one or more background ions transmitted to the reaction region by reacting the one or more background ions with a neutral organic chemical species in the reaction region;
extracting from the reaction region into a mass analyzer at least a portion of the ions with a m/z value in a selected m/z range and substantially excluding from extraction into the mass analyzer ions with a m/z value outside the selected m/z range.

2. The method of claim 1, wherein the one or more background ions transmitted to the reaction region comprise one or more of an adipate, sebacate, phthalate, phenyl phosphate, silicone, and their derivatives.

3. The method of claim 1, wherein the one or more background ions transmitted to the reaction region comprise cluster ions comprising one or more of water, methanol, acetonitrile, and acetic acid.

4. The method of claim 1, wherein the one or more background ions transmitted to the reaction region are positive ions and the neutral organic chemical species is a nucleophile.

5. The method of claim 1, wherein the one or more background ions transmitted to the reaction region are negative ions and the neutral organic chemical species is a electrophile.

6. The method of claim 1, wherein the neutral organic chemical species contains a disulfide functionality.

7. The method of claim 6, wherein the neutral organic chemical species comprises one or more of dimethyl disulfide and diethyl disulfide.

8. The method of claim 1, wherein the neutral organic chemical species comprises ethylene oxide.

9. The method of claim 1, wherein one or more of the one or more analytes of interest comprises one or more of a protein, peptide and small molecule pharmaceutical.

10. The method of claim 9, wherein one or more of the peptides are a cysteine containing peptide.

11. The method of claim 1, wherein the neutral organic chemical species has a pressure in the range between about 0.1 millitorr and about 760 torr in the reaction region during the step of changing the m/z value of one or more background ions transmitted to the reaction region.

12. The method of claim 1, wherein the ion source comprises a matrix assisted laser desorption ionization (MALDI) ion source.

13. The method of claim 1, wherein the ion source comprises an electrospray ionization (ESI) ion source.

14. The method of claim 1, wherein the selected m/z range is selected to substantially exclude reaction products of the background ions and neutral organic chemical species that comprise one or more or addition of one or more molecules of the organic chemical species to the background ion, addition of one or more fragments of the organic chemical species to the background ion, and background ion fragments.

15. The method of claim 1, wherein the step of extracting from the reaction region into a mass analyzer at least a portion of the ions with a m/z value in a selected m/z range and substantially excluding from extraction into the mass analyzer ions with a m/z value outside the selected m/z range comprises collecting at least a portion of the extracted ions in an ion trap.

16. A method for reducing chemical noise in a mass spectrometry instrument, comprising the steps of:
providing a mass spectrometer comprising a first mass filter and a second mass filter with a reaction region disposed between the first mass filter and the second mass filter, wherein the first mass filter is disposed between an ion source and the reaction region, and wherein the second mass filter is disposed between the reaction region and a detector;
operating the first mass filter as a high pass mass filter;
adding a neutral organic chemical species to the reaction region that preferentially reacts with one or more background ions relative to one or more analytes of interest;
operating the second mass filter as a bandpass filter to allow transmission of one or more analytes of interest to the detector.

17. The method of claim 16, wherein the neutral organic chemical species contains a disulfide functionality.

18. The method of claim 16, wherein the neutral organic chemical species has a pressure in the range between about 0.1 millitorr and about 760 torr in the reaction region during the reaction with one or more background ions.

19. A method for reducing chemical noise in a mass spectrometry instrument, comprising the steps of:
substantially excluding ions in an ion source below a selected mass-to-charge ratio value (m/z) from entering a reaction region while transmitting at least a portion of ions from the ion source with a m/z value above a selected m/z value to the reaction region, the ions in the source comprising one or more background ions and one or more analytes of interest;
colliding at least a portion of the transmitted ions with a neutral organic chemical species in the reaction region; and
extracting from the reaction region at least a portion of ions with a m/z value in a selected m/z range and substantially excluding from extraction ions with a m/z value outside the selected m/z range; wherein the neutral organic chemical species react with one or more background ions in the reaction region but does not substantially react with one or more analytes of interest transmitted to the reaction region.

20. The method of claim 19, wherein the neutral organic chemical species contains a disulfide functionality.

21. A method for reducing chemical noise in a mass spectrometry instrument, comprising the steps of:
substantially excluding ions in an ion source in a selected range of ion mobility values from entering a reaction region while transmitting at least a portion of ions from the ion source with an ion mobility value outside the selected range of ion mobility values to the reaction region, the ions in the source comprising one or more background ions and one or more analytes of interest;
changing the m/z value of one or more background ions transmitted to the reaction region by reacting the one or more background ions with a neutral organic chemical species in the reaction region;
extracting from the reaction region into a mass analyzer at least a portion of the ions with a m/z value in a selected m/z range and substantially excluding from extraction into the mass analyzer ions with a m/z value outside the selected m/z range.

22. The method of claim 21, wherein the one or more background ions transmitted to the reaction region comprise one or more of an adipate, sebecate, phthalate, phenyl phosphate, silicone, and their derivatives.

23. The method of claim 21, wherein the one or more background ions transmitted to the reaction region comprise cluster ions comprising one or more of water, methanol, acetonitrile, and acetic acid.

24. The method of claim 21, wherein the one or more background ions transmitted to the reaction region are positive ions and the neutral organic chemical species is a nucleophile.

25. The method of claim 21, wherein the one or more background ions transmitted to the reaction region are negative ions and the neutral organic chemical species is a elecrophile.

26. The method of claim 21, wherein the neutral organic chemical species contains a disulfide functionality.

27. The method of claim 26, wherein the neutral organic chemical species comprises one or more of dimethyl disulfide and diethyl disulfide.

28. The method of claim 21, wherein the neutral organic chemical species comprises ethylene oxide.

29. The method of claim 21, wherein one or more of the one or more analytes of interest comprises one or more of a protein, peptide and small molecule pharmaceutical.

30. The method of claim 29, wherein one or more of the peptides are a cysteine containing peptide.

31. The method of claim 21, wherein the neutral organic chemical species has a pressure in the range between about 0.1 millitorr and about 760 torr in the reaction region during the step of changing the m/z value of one or more background ions transmitted to the reaction region.

32. The method of claim 21, wherein the ion source comprises an atmospheric pressure ionization (API) ion source.

33. The method of claim 21, wherein the ion source comprises an electrospray ionization (ESI) ion source.

34. The method of claim 21, wherein the selected m/z range is selected to substantially exclude reaction products of the background ions and neutral organic chemical species that comprise one or more or addition of one or more molecules of the organic chemical species to the background ion, addition of one or more fragments of the organic chemical species to the background ion, and background ion fragments.

35. The method of claim 21, wherein the step of extracting from the reaction region into a mass analyzer at least a portion of the ions with a m/z value in a selected m/z range and substantially excluding from extraction into the mass analyzer ions with a m/z value outside the selected m/z range comprises collecting at least a portion of the extracted ions in an ion trap.

36. The method of claim 21, wherein the selected range of ion mobility values is a range of differential ion mobility values.

* * * * *